(12) United States Patent
Maheshwari et al.

(10) Patent No.: US 10,973,932 B2
(45) Date of Patent: Apr. 13, 2021

(54) PRECLINICAL MODEL OF NEONATAL NECROTIZING ENTEROCOLITIS

(71) Applicant: University of South Florida, Tampa, FL (US)

(72) Inventors: Akhil Maheshwari, Tampa, FL (US); Mohan Kumar Krishnan, Tampa, FL (US)

(73) Assignee: University of South Florida, Tampa, FL (US)

( * ) Notice: Subject to any disclaimer, the term of this patent is extended or adjusted under 35 U.S.C. 154(b) by 312 days.

(21) Appl. No.: 15/947,060

(22) Filed: Apr. 6, 2018

(65) Prior Publication Data
US 2018/0289841 A1    Oct. 11, 2018

Related U.S. Application Data

(60) Provisional application No. 62/616,220, filed on Jan. 11, 2018, provisional application No. 62/483,165, filed on Apr. 7, 2017.

(51) Int. Cl.
*A01K 67/02* (2006.01)
*A61K 49/00* (2006.01)
*G01N 33/50* (2006.01)

(52) U.S. Cl.
CPC .......... *A61K 49/0008* (2013.01); *A01K 67/02* (2013.01); *G01N 33/5008* (2013.01); *A01K 2207/12* (2013.01); *A01K 2207/15* (2013.01); *A01K 2207/20* (2013.01); *A01K 2207/30* (2013.01); *A01K 2227/105* (2013.01); *A01K 2267/03* (2013.01)

(58) Field of Classification Search
CPC ................ A01K 67/02; A01K 2207/12; A01K 2227/105; A01K 2267/03
See application file for complete search history.

(56) References Cited

PUBLICATIONS

Hod et al. Vox Sanguinis, (Jun. 2014) vol. 107, Supp. Suppl. 1, pp. 28. Abstract No. 3D-S20-02. Meeting Info: 33rd International Congress of the International Society of Blood Transfusion, in Conjunction with the 33rd Congress of the KSBT and the 2014 Congress of the Korean Hematology Societies. (Year: 2014).*
Dong et al. Advances in Hematology 2012 article id:924042, pp. 1-8, 2012 (Year: 2012).*
AlFaleh et al., "Association of packed red blood cell transfusion and necrotizing enterocolitis in very low birth weight infants," Journal of neonatal-perinatal medicine, 2014, 7: 193-198.
Amin et al., "Association between red cell transfusions and necrotizing enterocolitis," The journal of maternal-fetal & neonatal medicine, 2012, 25: 85-89.
Bak et al., "Analysis of the association between necrotizing enterocolitis and transfusion of red blood cell in very low birth weight preterm infants," Korean journal of pediatrics, 2013, 56: 112-115.
Baxi et al., "Necrotizing enterocolitis in infants with congenital heart disease: the role of red blood cell transfusions," Pediatric cardiology, 2014, 35: 1024-1029.
Benkoe et al., "Serum levels of interleukin-8 and gut-associated biomarkers in diagnosing necrotizing enterocolitis in preterm infants," J. Pediatr. Surg., 2014, 49: 1446-1451.
Ben-Othman et al., "Leishmania-mediated inhibition of iron export promotes parasite replication in macrophages," PLoS Pathog., 2014, 10: e1003901.
Blau et al., "Transfusion-related acute gut injury: necrotizing enterocolitis in very low birth weight neonates after packed red blood cell transfusion," J Pediatr, 2011, 158: 403-409.
Cholette et al., "Washing red blood cells and platelets transfused in cardiac surgery reduces postoperative inflammation and number of transfusions: results of a prospective, randomized, controlled clinical trial," Pediatric critical care medicine, 2012, 13: 290-299.
Christensen et al., "Antecedents of Bell stage III necrotizing enterocolitis," J Perinatol, 2010, 30: 54-57.
Christensen et al., "Is "transfusion-associated necrotizing enterocolitis" an authentic pathogenic entity?," Transfusion, 2009, Transfusion 50: 1106-1112.
Christensen et al., "Neonates presenting with bloody stools and eosinophilia can progress to two different types of necrotizing enterocolitis," J Perinatol, 2012, 32: 874-879.
Christensen et al., "Unique risks of red blood cell transfusions in very-low-birth-weight neonates: associations between early transfusion and intraventricular hemorrhage and between late transfusion and necrotizing enterocolitis," The journal of maternal-fetal & neonatal medicine, 2013, 26: Suppl 2, 60-63.
Curtis et al., "Mechanisms of transfusion-related acute lung injury (TRALI): anti-leukocyte antibodies." Critical care medicine, 2006, 34, S118.
Demirel et al., "Transfusion-associated necrotising enterocolitis in very low birth weight premature infants," Transfusion medicine, 2012, 22: 332-337.
Derienzo et al., "Feeding practices and other risk factors for developing transfusion-associated necrotizing enterocolitis," Early human development, 2014, 90: 237-240.
Detlefsen et al., "Necrotizing enterocolitis in premature twins with twin-to-twin transfusion syndrome," Eur J Pediatr Surg, 2008, 18: 50-52.
Elabiad et al., "Effect of birth weight on the association between necrotising enterocolitis and red blood cell transfusions in <=1500 g infants," BMJ open 3, 2013, e003823.
El-Dib et al., "Red blood cell transfusion, feeding and necrotizing enterocolitis in preterm infants," J Perinatol, 2011, 31: 183-187.
Eucker et al., "Development of a fluorescent microsphere technique for rapid histological determination of cerebral blood flow," Brain research, 2010, 1326: 128-134.

(Continued)

*Primary Examiner* — Marcia S Noble
(74) *Attorney, Agent, or Firm* — Meunier Carlin & Curfman LLC

(57) ABSTRACT

The disclosure provides methods of generating a murine model of neonatal necrotizing enterocolitis, whereby the generated murine animal exhibits at least one symptom of neonatal necrotizing enterocolitis. The disclosure also provides methods to measure transfusion effects on anemia and methods for identifying and isolating an agent useful for the treatment or prevention of neonatal necrotizing enterocolitis.

14 Claims, 30 Drawing Sheets

(56) References Cited

PUBLICATIONS

Garg et al., "Relationship between Packed Red Blood Cell Transfusion and Severe Form of Necrotizing Enterocolitis: A Case Control Study," Indian Pediatr, 2015, 52: 1041-1045.
Gilson et al., "A novel mouse model of red blood cell storage and posttransfusion in vivo survival," Transfusion, 2009, 49: 1546-1553.
Gordon et al., "Monocyte and macrophage heterogeneity," Nature reviews Immunology, 2005, 5: 953-964.
Hay et al., "Should we believe in transfusion-associated enterocolitis? Applying a GRADE to the literature," Semin Perinatol, 2017, 41: 80-91.
Hempel et al., "The Evidence-Based Evaluation of Iron Deficiency Anemia," The Medical clinics of North America, 2016, 100: 1065-1075.
Hod et al., "Transfusion of red blood cells after prolonged storage produces harmful effects that are mediated by iron and inflammation," Blood, 2010, 115: 4284-4292.
Huybregts et al., "The association of hemodilution and transfusion of red blood cells with biochemical markers of splanchnic and renal injury during cardiopulmonary bypass," Anesth Analg, 2009, 109: 331-339.
Hyung et al., "The relationship of red blood cell transfusion to intestinal mucosal injury in premature infants," Pediatr. Surg., 2016, 52: 1152-1155.
Jilling et al., "The roles of bacteria and TLR4 in rat and murine models of necrotizing enterocolitis," J. Immunol., 2006, 177: 3273-3282.
Josephson et al., "Do Red Cell Transfusions Increase the Risk of Necrotizing Enterocolitis in Premature Infants?," J Pediatr, 2010, 157: 972-978.
Kaca et al., "Hemoglobin, a newly recognized lipopolysaccharide (LPS)-binding protein that enhances LPS biological activity," J. Biol. Chem., 1994, 269: 25078-25084.
Kim et al., "A late-lineage murine neutrophil precursor population exhibits dynamic changes during demand-adapted granulopoiesis," Scientific reports, 2017, 7: 39804.
Leaphart et al., "A Critical Role for TLR4 in the Pathogenesis of Necrotizing Enterocolitis by Modulating Intestinal Injury and Repair," Journal of immunology, 2007, 179, 4808-4820.
Maheshwari et al., "Cytokines associated with necrotizing enterocolitis in extremely-low-birth-weight infants," Pediatr Res, 2014, 76, 100.
Maheshwari et al., "TGF-β2 suppresses macrophage cytokine production and mucosal inflammatory responses in the developing intestine," Gastroenterology, 2011, 140, 242-243.
Maheshwari, "Immunologic and Hematological Abnormalities in Necrotizing Enterocolitis," Clin Perinatol, 2015, 42: 567-585.
Mally et al., "Association of necrotizing enterocolitis with elective packed red blood cell transfusions in stable, growing, premature neonates," Am J Perinatol, 2006, 23: 451-458.
Marin et al., "Red blood cell transfusion-related necrotizing enterocolitis in very-low-birthweight infants: a near-infrared spectroscopy investigation," Transfusion, 2013, 53: 2650-2658.
Mohamed et al., "Transfusion associated necrotizing enterocolitis: a meta-analysis of observational data," Pediatrics, 2012, 129: 529-540.
MohanKumar et al., "Cytokines and growth factors in the developing intestine and during necrotizing enterocolitis," Semin. Perinatol, 2016, 41: 52-60.
MohanKumar et al., "Gut mucosal injury in neonates is marked by macrophage infiltration in contrast to pleomorphic infiltrates in adult: evidence from an animal model," Am J Physiol Gastrointest Liver Physiol, 2012, 303: G93-102.
MohanKumar et al., "Intestinal epithelial apoptosis initiates gut mucosal injury during extracorporeal membrane oxygenation in the newborn piglet," Laboratory investigation, a journal of technical methods and pathology, 2014, 94, 150-160.
MohanKumar et al., "Smad7 Interrupts TGF-β Signaling in Intestinal Macrophages and Promotes Inflammatory Activation of these Cells during Necrotizing Enterocolitis," Pediatr Res, 2016, 79, 951-961.
MohanKumar et al., "Trinitrobenzene Sulfonic Acid-induced Intestinal Injury in Neonatal Mice Activates Transcriptional Networks Similar to those seen in Human Necrotizing Enterocolitis," Pediatr Res, 2016, 81: 99-112.
Namachivayam et al., "Neonatal Mice with Necrotizing Enterocolitis-like Injury Develop Thrombocytopenia despite Increased Megakaryopoiesis," Pediatr Res, 2016.
Nanthakumar et al., "Regulation of intestinal ontogeny: effect of glucocorticoids and luminal microbes on galactosyltransferase and trehalase induction in mice," Glycobiology, 2005, 15: 221-232.
Neu et al., "Necrotizing enterocolitis," N Engl J Med, 2011, 364(19): 1877-1879.
Ng et al., "Host-response biomarkers for diagnosis of late-onset septicemia and necrotizing enterocolitis in preterm infants," J. Clin. Invest., 2010, 120: 2989-3000.
Nolan et al., "Quantification of mRNA using real-time RT-PCR," Nature protocols, 2006, 1: 1559-1582.
Oh et al., "Absorbance and redox based approaches for measuring free heme and free hemoglobin in biological matrices," Redox Biol, 2016, 9: 167-177.
O'Neill, Jr., "Neonatal necrotizing enterocolitis," Surg Clin North Am, 1981, 61: 1013-1022.
Pammi et al., "Intestinal dysbiosis in preterm infants preceding necrotizing enterocolitis: a systematic review and meta-analysis," Microbiome, 2017, 5: 31.
Patel et al., "Association of Red Blood Cell Transfusion, Anemia, and Necrotizing Enterocolitis in Very Low-Birth-Weight Infants," JAMA, 2016, 315: 889-897.
Patel et al., "Causes and timing of death in extremely premature infants from 2000 through 2011," N Engl J Med, 2015, 372, 331-340.
Paul et al., "Increased odds of necrotizing enterocolitis after transfusion of red blood cells in premature infants," Pediatrics, 2011, 127: 635-641.
Pearson et al., "Scanning electron microscopy of early postmortem artefacts in the small intestine of a neonatal calf," British journal of experimental pathology, 1978, 59, 499-503.
Rausen et al., "Haptoglobin patterns in cord blood serums," Nature, 1961, 191: 717.
Remon et al., "Depth of bacterial invasion in resected intestinal tissue predicts mortality in surgical necrotizing enterocolitis," J Perinatol, 2015, 35: 755-762.
Rosebraugh et al., "A mathematical modeling approach to quantify the role of phlebotomy losses and need for transfusions in neonatal anemia," Transfusion, 2013, 53: 1353-1360.
Salsbury, "Anemia of prematurity," Neonatal network, 2001, 20, 13-20.
Sampath et al., "The NFKB1 (g.-24519delATTG) variant is associated with necrotizing enterocolitis (NEC) in premature infants," J Surg Res, 2011, 169, e51.
Scheifele et al., "Rapid postmortem gut autolysis in infant rats: a potential problem for investigators," Can. J. Vet. Res., 1987, 51: 404-406.
Schreiber et al., "Intestinal monocytes and macrophages are required for T cell polarization in response to Citrobacter rodentium," J. Exp. Med., 2013, 210: 2025-2039.
Schutzman et al., "Glucose-6-phosphate dehydrogenase deficiency: another risk factor for necrotizing enterocolitis?," J Pediatr, 2007, 151: 435-437.
Sharma et al., "Impact of gestational age on the clinical presentation and surgical outcome of necrotizing enterocolitis," J Perinatol, 2006, 26, 342-347.
Shiou et al., "Erythropoietin protects intestinal epithelial barrier function and lowers the incidence of experimental neonatal necrotizing enterocolitis," The Journal of biological chemistry, 2011, 286: 12123-12132.
Singh et al., "Association of necrotizing enterocolitis with anemia and packed red blood cell transfusions in preterm infants," J Perinatol, 2011, 31: 176-182.

(56) References Cited

PUBLICATIONS

Snippert et al., "Slide preparation for single-cell-resolution imaging of fluorescent proteins in their three-dimensional near-native environment," Nature protocols, 2011, 6, 1221-1228.

Stritzke et al., "Transfusion-associated necrotising enterocolitis in neonates," Arch Dis Child Fetal Neonatal Ed, 2013, 98: F10-14.

Tao et al., "Meta-analysis of post-transfusion necrotizing enterocolitis in neonates," Zhonghua er ke za zhi = Chinese journal of pediatrics, 2013, 51, 336-339.

Thorpe et al., "Autolysis and post-mortem bacteriological changes in the alimentary tract of the pig," The Journal of pathology and bacteriology, 1967, 93, 601-610.

Ververidis et al., "The clinical significance of thrombocytopenia in neonates with necrotizing enterocolitis," J Pediatr Surg, 2001, 36: 799-803.

Walthall et al., "Postnatal development of the gastrointestinal system: a species comparison," Birth Defects Res. B Dev. Reprod. Toxicol., 2005, 74: 132-156.

Yang et al., "Arginase regulates red blood cell nitric oxide synthase and export of cardioprotective nitric oxide bioactivity," Proc Natl Acad Sci U S A, 2013, 110: 15049-15054.

Yee et al., "Incidence and timing of presentation of necrotizing enterocolitis in preterm infants," Pediatrics, 2012, 129: e298-304.

Zaynagetdinov et al., "Identification of myeloid cell subsets in murine lungs using flow cytometry," Am. J. Respir. Cell Mol. Biol., 2013, 49: 180-189.

Zhong et al., "Role of lipid peroxidation derived 4-hydroxynonenal (4-HNE) in cancer: focusing on mitochondria," Redox biology, 2015, 4: 193-199.

Zhou et al., "Peptide-siRNA nanocomplexes targeting NF-kappaB subunit p65 suppress nascent experimental arthritis," J. Clin. Invest., 2014, 124: 4363-4374.

\* cited by examiner

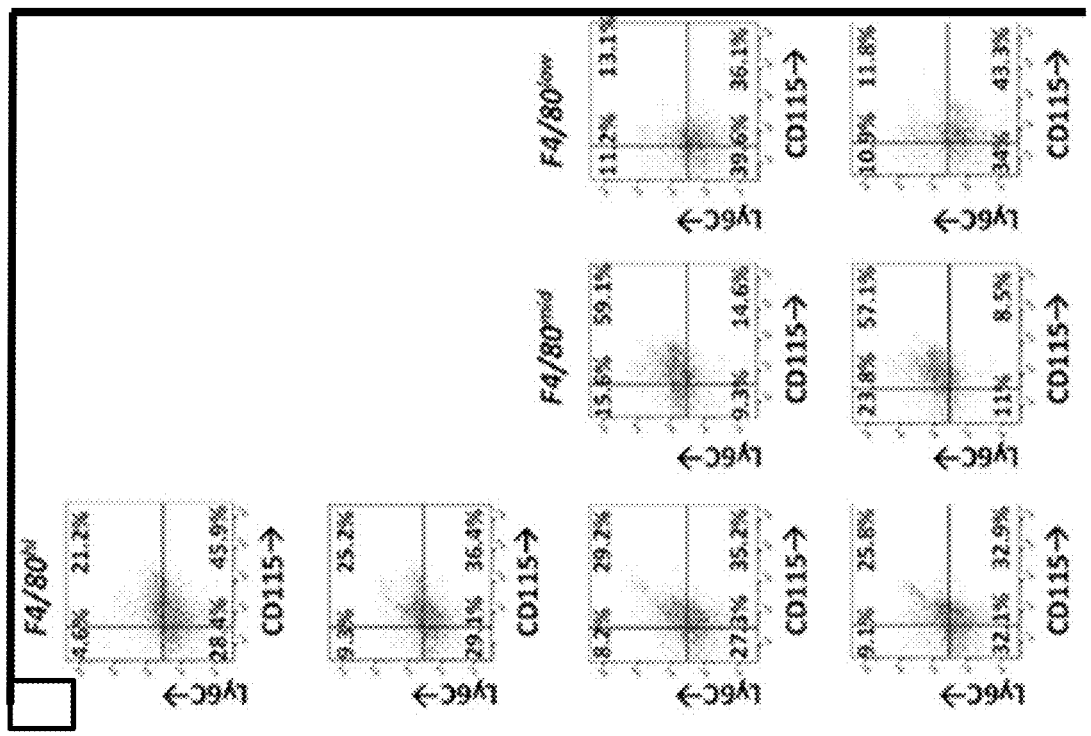
FIG. 4C
FIG. 4B
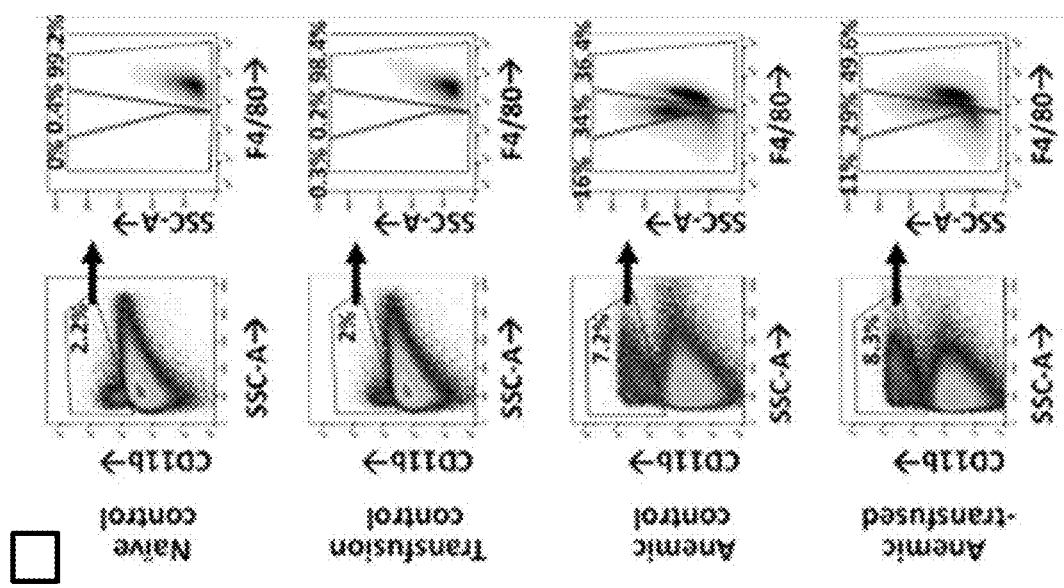
FIG. 4A

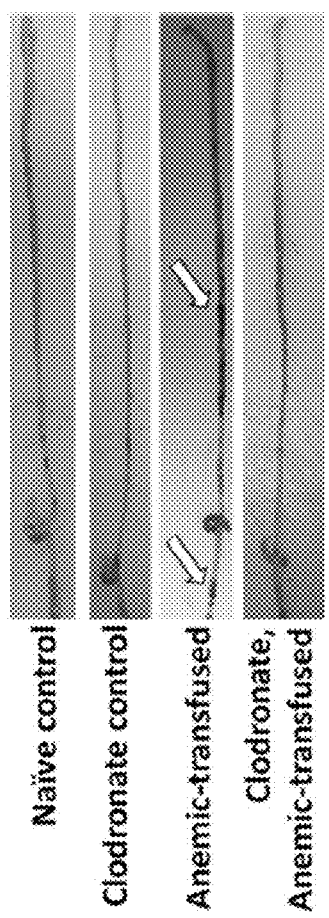
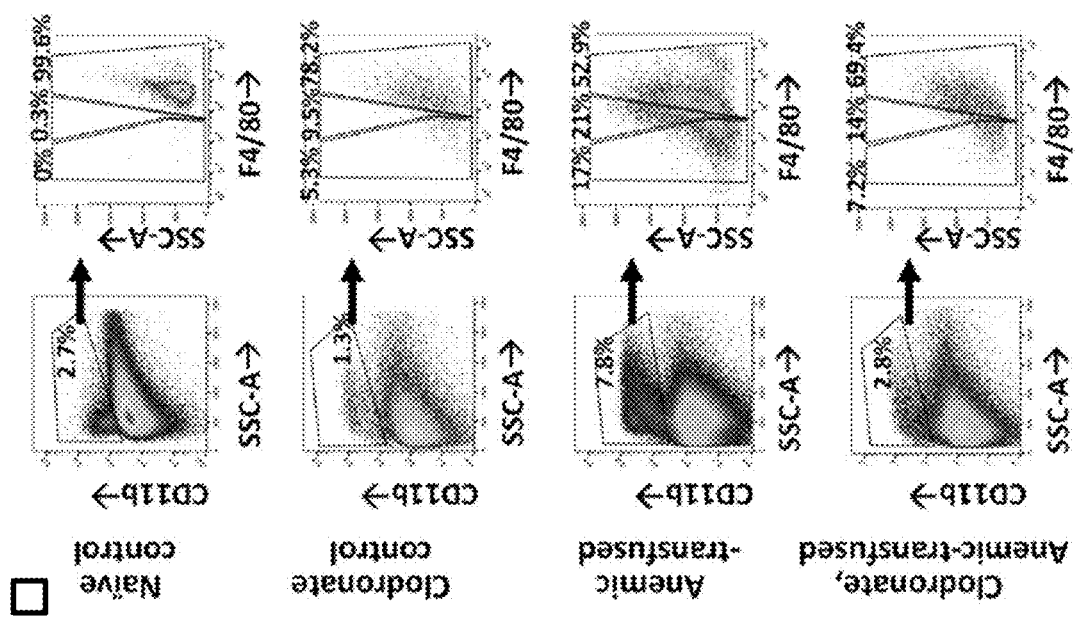
FIG. 7B
FIG. 7A

PRECLINICAL MODEL OF NEONATAL NECROTIZING ENTEROCOLITIS

CROSS REFERENCE TO RELATED APPLICATIONS

This application claims priority to U.S. Provisional Application No. 62/483,165, filed Apr. 7, 2017, and U.S. Provisional Application No. 62/616,220, filed Jan. 11, 2018, which are incorporated herein by reference in their entirety.

STATEMENT OF FEDERALLY-SPONSORED RESEARCH

This invention was made with government support under HL124078 awarded by the National Institutes of Health. The government has certain rights in the invention.

TECHNICAL FIELD

The present disclosure relates to a murine model of neonatal necrotizing enterocolitis, and methods of preparing and using said murine model.

BACKGROUND

Necrotizing enterocolitis (NEC) is an inflammatory bowel necrosis of premature infants, and is a leading cause of mortality in infants born between 22-28 weeks' gestation. One-third of all cases of NEC occur within 48 hours after receiving a red blood cell (RBC) transfusion, but the underlying mechanisms are unclear. A major barrier to progress in developing new treatments for NEC is the lack of understanding of its mechanisms, which in turn, is secondary to a lack of robust preclinical models. In the last decade, more than 20 retrospective clinical studies and the meta-analysis of observational data in these studies have identified an association between red blood cell transfusions and necrotizing enterocolitis. These studies show important center-based differences in demographics, severity of illness, and in the baseline rate of NEC, but there are several common elements: (a) 25-40% of all cases of NEC had received an RBC transfusion in the preceding 48 hours; (b) infants with transfusion-associated NEC were more premature and developed NEC at a later postnatal age than NEC unrelated to transfusions; and (c) many cases had received multiple RBC transfusions. Despite the consistency of this association, the retrospective, observational design of these studies has left unaddressed concerns about causality and the overall quality of evidence. There has been a long-standing need for a robust preclinical model to investigate this association.

SUMMARY OF THE INVENTION

The present disclosure provides a method for generating a murine model of neonatal necrotizing enterocolitis. The method comprises: inducing anemia in a murine animal to generate an anemic murine animal; and administering at least one transfusion of red blood cells to the anemic murine animal, whereby the anemic murine animal exhibits at least one symptom of neonatal necrotizing enterocolitis.

The present disclosure provides a method to measure transfusion effects on anemia in a murine model. The method comprises: inducing anemia in a murine animal to generate an anemic murine animal; administering at least one transfusion of red blood cells to the anemic murine animal, whereby the murine animal exhibits at least one symptom of neonatal necrotizing enterocolitis; and measuring at least one of inflammatory markers or cytokines, intestinal mucosa or epithelia inflammation, macrophage infiltration of intestinal mucosa, intestinal mucosal lesions, intestinal coagulation necrosis, intestinal interstitial hemorrhages, intestinal crypt villus disruption, focal intestinal epithelia disruption, other bowel injury, or combinations thereof, before and after the transfusion of red blood cells thereby measuring the effects of transfusion on anemia.

The present disclosure provides a method for identifying and isolating an agent useful for the prevention of neonatal necrotizing enterocolitis. The method comprises: inducing anemia in a murine animal to generate an anemic murine animal; administering a candidate agent to the anemic murine animal thereby generating a treated anemic murine animal; administering at least one transfusion of red blood cells to the treated anemic murine animal, whereby the treated anemic murine animal exhibits at least one symptom of neonatal necrotizing enterocolitis; measuring at least one neonatal necrotizing enterocolitis symptoms in the treated anemic murine animal and identifying the candidate agent as useful for the prevention of neonatal necrotizing enterocolitis when the neonatal necrotizing enterocolitis symptom in the treated anemic murine animal are improved or delayed in the treated anemic murine animal, as compared to an untreated anemic murine animal that has been administered a transfusion of red blood cells, and wherein the at least one neonatal necrotizing enterocolitis symptoms comprises intestinal mucosa or epithelia inflammation, macrophage infiltration of intestinal mucosa, intestinal mucosal lesions, intestinal coagulation necrosis, intestinal interstitial hemorrhages, intestinal crypt villus disruption, focal intestinal epithelia disruption, other bowel injury, or combinations thereof.

The present disclosure provides a murine animal exhibiting at least one symptom of neonatal necrotizing enterocolitis produced by the method as described above.

The present disclosure provides a method for identifying an agent for treating neonatal necrotizing enterocolitis. The method comprises: administering a candidate agent to the murine animal of claim 17; measuring at least one symptom of neonatal necrotizing enterocolitis symptoms before and after the candidate agent is administered to the murine animal, wherein the at least one symptom of neonatal necrotizing enterocolitis symptoms comprises intestinal mucosa or epithelia inflammation, macrophage infiltration of intestinal mucosa, intestinal mucosal lesions, intestinal coagulation necrosis, intestinal interstitial hemorrhages, intestinal crypt villus disruption, focal intestinal epithelia disruption, other bowel injury, or combinations thereof; and identifying the candidate agent as useful for treating neonatal necrotizing enterocolitis when there is an improvement in the neonatal necrotizing enterocolitis symptom after the candidate agent is administered to the murine animal.

Other aspects of the invention will become apparent by consideration of the detailed description and accompanying drawings.

BRIEF DESCRIPTION OF THE DRAWINGS

FIGS. 4A-4D show macrophage infiltration in RBC transfusion-associated NEC-like injury. Representative scatter plots from control and anemic-transfused mice show that the CD11b+ myeloid cell fraction was enriched in anemic and anemic-transfused mice and clustered into discrete F4/80$^{hi}$, F4/80$^{mid}$, F4/80$^{low}$ populations (FIG. 4A). F4/80$^{hi}$ cells were CD115+ and included Ly6C$^{hi}$ and Ly6C$^{low}$ subpopulations, the F4/80mid macrophage population in the anemic and anemic-transfused mice were CD115+Ly6C$^{hi}$, and the F4/80$^{low}$ fraction included CD115+Ly6Clo monocytes along with some CD115−Ly6C$^{low}$ cells (FIG. 4B). F4/80$^{low}$ fraction included some neutrophils, comprised of Ly6G$^{mid}$ Ly6B+ late-lineage neutrophil precursors (FIG. 4C, box on left) and a few mature Ly6G$^{hi}$ Ly6B+ neutrophils (FIG. 4C, box on right). Fluorescence photomicrographs (ileum, colon; magnification 800×) showed scattered F4/80+ macrophages (FIG. 4D, open arrows) in naïve control and transfusion control. Numerous Ly6C+ cells (FIG. 4D, solid arrows) were seen in anemic control and the anemic-transfused intestine. Scatter plots on right summarize the number of Ly6C+ and F4/80+ cells in each group. Kruskal-Wallis H test with Dunn's post-test, † P<0.001 vs. naïve control. Data represent 10 mice per group.

FIG. 6A shows the expression of cytokines, FIG. 6B shows expression of genes in the Toll-like receptor activated pathway, and FIG. 6C shows expression of genes in NF-κB signaling. Data is normalized against 18S ribosomal RNA. Crossing threshold values were compared by the Kruskal-Wallis H test, * P<0.05 vs. naïve control. N=8 mice per group.

FIGS. 7A-7G show that macrophage depletion prevents RBC transfusion-associated NEC-like injury. Representative scatter plots from naïve control, anemic-transfused, and corresponding clodronate-treated groups show that clodronate depleted F4/80$^{hi}$ macrophages in naïve control and both F4/80$^{hi}$ and F4/80$^{mid}$ populations in anemic-transfused mice (FIG. 7A). Photographs show intestinal injury in an anemic-transfused pup (FIG. 7B, arrows) and the absence of injury in a clodronate-treated pup. Kaplan-Meier curves show the onset of NEC-like injury in control and anemic-transfused pups (FIG. 7C). Clodronate treatment of anemic-transfused mice was protective; Mantel-Cox log-rank test, ** P<0.01. Scatter plots summarize the severity of bowel injury in anemic-transfused vs. clodronate-treated anemic-transfused mice (FIG. 7D). N=3 each in naïve, transfusion, and anemic controls, 5 clodronate control, and 8 each in anemic-transfused and clodronate-treated anemic-transfused groups. Two clodronate-treated anemic-transfused mice died within 1 hr of presumed procedure-related causes and were excluded; Mann-Whitney U test, * P<0.05. Representative scatter plots from CSF1R-DTR/mCherry×Lyz2-cre mice show that administration of diphtheria toxin (DT) depleted the F4/80$^{mid}$ CD115+Ly6C$^{hi}$ macrophages in the anemic intestine (FIG. 7E). Kaplan-Meier curves below show that DT-mediated macrophage depletion in these mice was protective; Mantel-Cox log-rank test,  P<0.01. Photographs show intestinal injury in an anemic-transfused pup (FIG. 7F, arrows) and the absence of injury in a DT-treated pup. Scatter plots summarize the severity of bowel injury in the control vs. DT-treated anemic-transfused CSF1R-DTR/mCherry×Lyz2-cre mice (FIG. 7G). N=6 anemic-transfused but no DT, 4 anemic-transfused treated with DT; Mann-Whitney U test,  P<0.01.

FIGS. 9H-9I show ileal and colonic injury following RBC transfusions in pups inoculated with either cecal flora from adult mice (with scant Gammaproteobacteria) or with *Serratia marcescens* on P7. N=15 mice colonized with cecal flora, 21 colonized with *Serratia;* Mann-Whitney U test, * P<0.05.

DETAILED DESCRIPTION

Figure 1A:
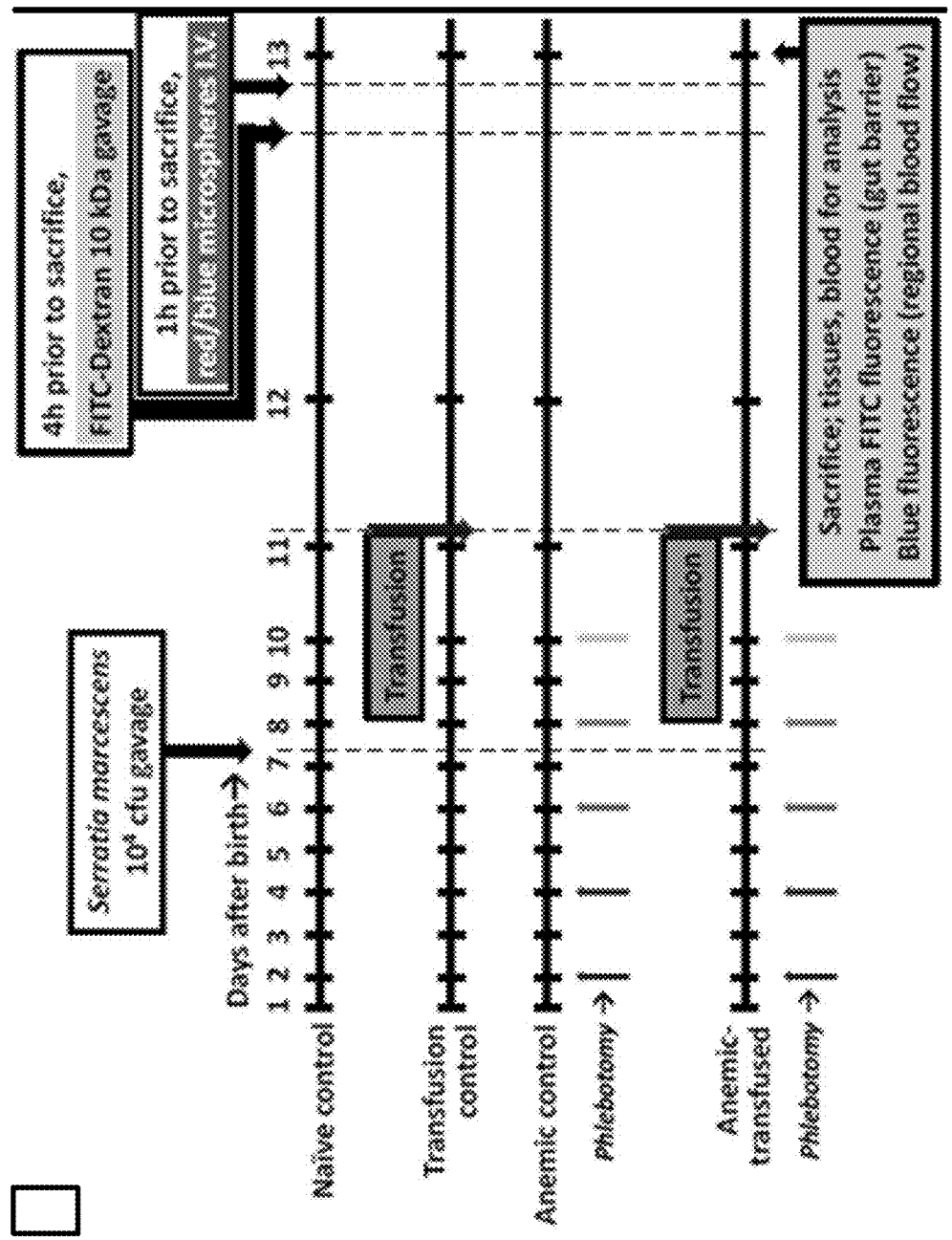
FIGS. 1A-1C show the neonatal murine model of RBC transfusion-associated NEC-like injury. A schematic (FIG. 1A) shows the sequence of interventions in naïve control, transfusion control, anemic control, and anemic-transfused mice. Line diagrams (means±standard error) show the longitudinal change in the hematocrits in control vs. anemic mice subjected to repeated phlebotomy (FIG. 1B). Scatter column plots (FIG. 1C, means±standard deviation) show the hematocrit values in the four study groups on P12 (24 hrs after transfusions). Data in panels (FIG. 1B) and (FIG. 1C) represent N=42 in naïve control, 21 in transfusion control, 18 in anemic control, and 21 in anemic-transfused groups. Kruskal-Wallis H test with Dunn's post-test, * P<0.05, † (dagger) P<0.001 vs. naïve control.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

The present disclosure relates to neonatal murine models of transfusion-associated neonatal necrotizing enterocolitis (NEC) that have been developed based on a detailed investigation of RBC transfusion-associated NEC and its mechanisms in the murine models, as described herein. Anemia and red blood cell (RBC) transfusion-related gut injury have been shown to have a correlation with neonatal NEC. Anemia potentially compromises mucosal integrity with subsequent poor healing, and this injury may be augmented by yet unknown factors associated with RBC transfusions. The disclosed murine models were developed based on the inventor's discovery that red blood cell (RBC) transfusions triggered NEC in the presence of severe anemia through a hypoxia-reoxygenation mechanism. In particular, RBC transfusions triggered NEC-like bowel injury in mouse pups with severe anemia, but were not injurious when administered in mice with normal hematocrit. Severe anemia caused a low-grade inflammatory state in the intestinal mucosa with macrophage infiltration, and subsequent RBC transfusions activated these cells to cause bowel injury. Consistent with existing clinical studies, transfusion-associated NEC-like injury was more likely and more severe in pups with severe (vs. moderate) anemia and in pups that had been severely anemic for a longer duration. The onset of NEC-like injury between 18-28 hrs after RBC transfusions is consistent with the typical course of transfusion-associated NEC in human infants. This is the first report of a preclinical model of transfusion-associated NEC.

The emphasis on anemia, rather than on the RBC transfusions, was based on several emerging lines of evidence: (a) RBC transfusions can trigger intestinal injury during cardiopulmonary bypass in severely anemic patients; (b) NEC is associated with diverse conditions marked by anemia, including glucose-6-phosphate dehydrogenase deficiency, hemolytic disease of the newborn, and in donor twins in twin-to-twin transfusion syndrome; and (c) transfusion-associated NEC is usually a late event that occurs beyond 4 weeks of postnatal age, when these infants are also likely to be anemic. The effect of anemia in risk-stratification for transfusion-associated NEC has been described in at least 2 clinical studies. As disclosed herein, severe anemia was shown to lead to the development of a low-grade inflammatory state in the intestine with prominent macrophage infiltration. Subsequent RBC transfusions activated these macrophages and led to the development of NEC-like injury.

For example, anemic-transfused pups generated using the disclosed methods developed NEC-like injury involving the ileocecal and mid-colonic regions. Consistent with these histopathological findings, evidence of epithelial injury and mucosal barrier disruption was detected in these mice. The severity of transfusion-associated bowel injury increased with the severity and duration of anemia, which was likely to have accentuated the inflammatory changes in the anemic intestine and thus predisposed to transfusion-induced bowel injury. The inflammatory response and intestinal injury was associated with macrophage infiltration and increased expression of inflammatory cytokines, TLRs and NF-κB pathway genes. The anemic intestine also showed increased expression of CXCL5 and TNF. CXCL5 plays an important role in recruiting macrophages to NEC lesions. TNF has also been identified as a major upstream regulator of transcriptional networks activated in NEC.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are hereby incorporated by reference in their entirety. The materials, methods, and examples disclosed herein are illustrative only and not intended to be limiting.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

"About" is used synonymously herein with the term "approximately." Illustratively, the use of the term "about" indicates that values slightly outside the cited values, namely, plus or minus 10%. Such values are thus encompassed by the scope of the claims reciting the terms "about" and "approximately."

The use of the terms "a" and "an" and "the" and "at least one" and similar referents in the context of describing the invention (especially in the context of the following claims) are to be construed to cover both the singular and the plural, unless otherwise indicated herein or clearly contradicted by context.

The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context.

The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein.

The term "anemia" is used herein to refer to a condition wherein the blood has less than the normal number of red blood cells or less than the normal quantity of hemoglobin in the blood; the oxygen-carrying capacity of the blood is, therefore, decreased.

The term "anemic" is used herein to refer to one suffering from anemia.

The term "hematocrit" is used herein to refer to the volume percentage of red blood cells in blood. The measure of hematocrit levels can indicate possible disease; an abnormally low hematocrit may suggest anemia. For example, normal hematocrit levels in mice can be about 50% whereas values less than 30% can indicate anemia.

The terms "leukoreduced" and "leukoreduction" as used interchangeably herein refer to the removal of white blood cells, or leukocytes, from the blood or blood components being supplied for a transfusion.

"Necrotizing enterocolitis," "neonatal necrotizing enterocolitis," and "NEC" as used interchangeably herein refer to a medical condition where a portion of the bowel dies. The condition typically occurs in newborns that are either premature or otherwise unwell and the timing of onset is generally inversely proportional to the gestational age of the baby at birth (i.e., the earlier a baby is born, the later signs of NEC are seen).

The term "phlebotomy" is used herein to refer to a procedure that removes blood from the body.

The term "postnatal" is used herein to refer to the period that begins immediately after birth. For example, postnatal day 5, refers to the fifth day after birth.

The terms "red blood cells" and "RBCs" as used interchangeably herein refer to the type of blood cell which contains hemoglobin to delivery oxygen to the tissues of the body. Nearly half of the volume of blood is red blood cells.

The term "symptoms" is used herein to refer to any one or more pathological manifestations of a disease known in the art. Such manifestations may be overt physical characteristics or clinical measurements of biological molecule profiles.

The term "transfusion" is used herein to refer to an act of transferring blood, blood products, or other fluid into the circulatory system of a person or animal. Transfusions are used for various medical conditions to replace lost components of the blood.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

For the recitation of numeric ranges herein, each intervening number there between with the same degree of precision is explicitly contemplated. For example, for the range of 6-9, the numbers 7 and 8 are contemplated in addition to 6 and 9, and for the range of 6.0-7.0, the number 6.0, 6.1, 6.2, 6.3, 6.4, 6.5, 6.6, 6.7, 6.8, 6.9, and 7.0 are explicitly contemplated.

2. Murine Model of NEC

One embodiment of the present invention is a murine animal exhibiting at least one symptom of neonatal necrotizing enterocolitis prepared by the methods disclosed herein. The murine animal may exhibit at least one symptom of neonatal necrotizing enterocolitis comprising inflammation of intestinal mucosa or epithelia, macrophage infiltration of intestinal mucosa, intestinal mucosal lesions, intestinal coagulation necrosis, intestinal interstitial hemorrhages, intestinal crypt villus disruption, focal intestinal epithelia disruption, induction of inflammatory markers or cytokines, other bowel injury, or combinations thereof.

Transfusion-associated murine NEC-like injury showed a strong resemblance to human NEC, including regional predilection for the ileocecal and mid-colonic regions, histopathological changes such as coagulation necrosis and macrophage infiltration (which show signs of inflammatory activation), increased circulating markers such as Cxcl2, C-reactive protein, and serum amyloid A, and induction of cytokines such as IL1B, TNF, CCL2, CCL3, CCL5, and CXCL5. The activation of TLR4, MYD88, and the NF-κB pathway genes was also consistent with previous reports of human NEC. Macrophage infiltration in human NEC and in trinitrobenzene sulfonate (TNBS)-induced murine NEC-like injury was previously described. The similarity in pathoanatomy, inflammatory response, and the transcriptional changes in transfusion-associated murine NEC-like injury and human NEC provide validation for the murine models in the present study. At the same time, the strong resemblance between human NEC, TNBS-induced murine NEC-like injury, and the current model of transfusion-associated NEC-like injury also lend credence to the contention that the pathoanatomy of NEC represents the generic injury response of the intestine during a certain developmental epoch and does not change with specific causal triggers. This postulation is supported by increasing evidence that the incidence of NEC in premature infants peaks at a postmenstrual age (gestational age at birth+postnatal age in weeks) equivalent to 32 weeks' gestation.

3. Methods for Generating a Murine Model of NEC

The present disclosure provides methods for generating a murine model of neonatal necrotizing enterocolitis. The disclosed methods involve inducing anemia in a murine animal, such as a mouse, to generate an anemic murine animal, such as an anemic mouse, and administering at least one transfusion of red blood cells to the anemic murine animal whereby the anemic murine animal exhibits at least one symptom of neonatal necrotizing enterocolitis. The murine models prepared in accordance with the teachings herein exhibit at least one symptom analogous to human patients suffering from neonatal necrotizing enterocolitis and thus provide a murine model of human neonatal necrotizing enterocolitis. The murine models prepared in accordance with the teachings herein are useful in studying the manifestation, penetration and progression of neonatal necrotizing enterocolitis in humans. In addition, the murine models are also useful for testing new methods and products for the diagnosis and/or treatment of neonatal necrotizing enterocolitis.

In some embodiments, the murine models prepared using the disclosed methods may exhibit at least one symptom of neonatal necrotizing enterocolitis such as those known in the art. For example, such manifestations may be overt physical characteristics or clinical measurements of biological molecules or markers. In some embodiments, the at least one symptom of neonatal necrotizing enterocolitis may include, but is not limited to, inflammation of intestinal mucosa or epithelia, macrophage infiltration of intestinal mucosa, intestinal mucosal lesions, intestinal coagulation necrosis, intestinal interstitial hemorrhages, intestinal crypt villus disruption, focal intestinal epithelia disruption, induction of inflammatory markers or cytokines, other bowel injury, or combinations thereof. In some embodiments, the induction of inflammatory markers or cytokines may include, but is not limited to, increases in circulating markers, such as Cxcl2, C-reactive protein, and serum amyloid A, induction of cytokines such as IL1B, TNF, CCL2, CCL3, CCL5, and CXCL5 and activation of TLR4, MYD88, and the NF-κB pathway genes.

a. Anemia

Embodiments of the methods disclosed herein include inducing anemia in a murine animal to generate an anemic murine animal. In some embodiments, the murine animal is made anemic by phlebotomy. In some embodiments, the murine animal is made anemic by treatment with exogenous factors, such as serpentine, fungal poison, saponins, arsenic, hydrogen, benzene, phenylhydrazine, phosphorus, nitrosourea derivatives and others. In some embodiments, the murine animal is a transgenic murine animal characterized by having anemia, such as an erythropoietin knock-out mouse, an alpha-globin knock-out mouse, a beta-globin knock-out mouse, a mouse carrying a mutational defect in the erythropoietin gene, a mouse carrying a mutational defect in the alpha-globin gene, a mouse carrying a mutational defect in the β-globin gene, or a mouse with a knock-out or mutation in at least one of the RBC cytoskeleton genes. In some embodiments, the murine animal is an erythropoietin knock-out/flox mouse, which is heterozygous and anemic. In some embodiments of the invention, the murine animal may be made anemic by administering at least one phlebotomy to the murine animal after postnatal day 1. In some embodiments, the at least one phlebotomy may be administered to the murine animal between postnatal day 1 and postnatal day 15. For example, at least one phlebotomy may be administered to the murine animal between postnatal day 1 and postnatal day 15, between postnatal day 1 and postnatal day 12, between postnatal day 1 and postnatal day 10, between postnatal day 1 and postnatal day 9, between postnatal day 1 and postnatal day 8, between postnatal day 1 and postnatal day 7, between postnatal day 1 and postnatal day 6, between postnatal day 2 and postnatal day 15, between postnatal day 2 and postnatal day 12, between postnatal day 2 and postnatal day 10, between postnatal day 2 and postnatal day 9, between postnatal day 2 and postnatal day 8, between postnatal day 2 and postnatal day 7, between postnatal day 2 and postnatal day 6, between postnatal day 3 and postnatal day 15, between postnatal day 3 and postnatal day 12, between postnatal day 3 and postnatal day 10, between postnatal day 3 and postnatal day 9, between postnatal day 3 and postnatal day 8, between postnatal day 3 and postnatal day 7, between postnatal day 3 and postnatal day 6, between postnatal day 4 and postnatal day 15, between postnatal day 4 and postnatal day 12, between postnatal day 4 and postnatal day 10, between postnatal day 4 and postnatal day 9, between postnatal day 4 and postnatal day 8, between postnatal day 4 and postnatal day 7, between postnatal day 4 and postnatal day 6, between postnatal day 5 and postnatal day 15, between postnatal day 5 and postnatal day 12, between postnatal day 5 and postnatal day 10, between postnatal day 5 and postnatal day 9, between postnatal day 5 and postnatal day 8, between postnatal day 5 and postnatal day 7, between postnatal day 5 and postnatal day 6, between postnatal day 6 and postnatal day 15, between postnatal day 6 and postnatal day 12, between postnatal day 6 and postnatal day 10, between postnatal day 6 and postnatal day 9, between postnatal day 6 and postnatal day 8, or between postnatal day 6 and postnatal day 7. In some embodiments, the at least one phlebotomy may be administered to the murine animal at postnatal day 1, at postnatal day 2, at postnatal day 3, at postnatal day 4, at postnatal day 5, at postnatal day 6, at postnatal day 7, at postnatal day 8, at postnatal day 9, at postnatal day 10, at postnatal day 12, or at postnatal day 15.

In some embodiments, at least one, at least two, at least three, at least four, at least five, at least six, or at least seven phlebotomies are administered to the murine animal. In some embodiments, between about 1 and about 7, between about 1 and about 6, between about 1 and about 5, between about 1 and about 4, between about 1 and about 3, between about 1 and about 2, between about 2 and about 7, between about 2 and about 6, between about 2 and about 5, between about 2 and about 4, between about 2 and about 3, between about 3 and about 7, between about 3 and about 6, between about 3 and about 5, between about 3 and about 4, between about 4 and about 7, between about 4 and about 6, between about 4 and about 5, between about 5 and about 7, between about 5 and about 6, or between about 6 and about 7 phlebotomies are administered to the murine animal. In some embodiments, between about three and about six phlebotomies are administered to the murine animal. In some embodiments 5 phlebotomies are administered to the murine animal. In some embodiments, the phlebotomies are administered separately by at least one day from each other, in other words, a phlebotomy is administered at least one day after a previous phlebotomy. In some embodiments, one phlebotomy is administered at postnatal day 2, at postnatal day 4, at postnatal day 6, at postnatal day 8, and at postnatal day 10.

In some embodiments, the at least one phlebotomy includes withdrawing blood from any vein or blood vessel in the murine animal. For example, the blood may be withdrawn from a venus plexus, a superficial temporal vein, a facial vein or a tail vein. In some embodiments, the blood is withdrawn from a facial vein. In some embodiments, the at least one phlebotomy collects between about 10 μL and about 100 μL of blood. In some embodiments, at least about 40 μL of blood is collected.

The presence or absence of anemia can be determined by monitoring hematocrit levels which provide measurements of the volume percentage of red blood cells in the blood. For example, the average normal hematocrit in mouse pups can be in the range of 40 to 50%. In some embodiments, a condition of anemia occurs when the hematocrit levels are less than approximately 30%. In some embodiments, the hematocrit levels of the anemic murine animal may be less than about 30%, less than about 25%, less than about 20% or less than about 15%. In some embodiments, the hematocrit may be between about 15 and about 20%, about 20 and about 25%, or about 25 and about 30%.

In some embodiments, the anemic murine animal can have a hematocrit less than 30% prior to the at least one transfusion of red blood cells. In some embodiments, the anemic murine animal can have a hematocrit between about 15 and about 20%, about 20 and about 25%, or about 25 and about 30% prior to the at least one transfusion of red blood cells. In some embodiments, the anemic murine animal can have a hematocrit less than 30%, less than 25%, less than 20%, or less than 15% prior to the at least one transfusion of red blood cells.

b. Red Blood Cell Transfusions

Embodiments of the methods disclosed herein include administering at least one transfusion of red blood cells (RBCs) to the anemic murine animal. RBC transfusions are commonly used to improve oxygen delivery in subjects with anemia by replenishing the blood with hemoglobin containing red blood cells. In some embodiments, between about 1 and 5 transfusions of red blood cells are administered to the anemic murine animal. In some embodiments, between about 1 and 5, between about 1 and 4, between about 1 and 3, between about 1 and 2, between about 2 and 5, between about 2 and 4, or between about 2 and 3 transfusions of RBCs are administered to the anemic murine animal. In some embodiments, at least 1, at least 2, at least 3, at least 4, or at least 5 transfusions of RBCs are administered to the anemic murine animal. In some embodiments, one transfusion of red blood cells is administered to the murine animal.

In some embodiments, the at least one transfusion of RBCs may be administered to the murine animal on or after postnatal day 10. In some embodiments of the invention, the at least one transfusion of RBCs may be administered to the murine animal on postnatal day 10, on postnatal day 11, on postnatal day 12 or on postnatal day 13. In one embodiment at least one transfusion of RBCs is administered to the murine animal on postnatal day 11.

In certain embodiments, the RBCs include leukoreduced RBCs. Red blood cells are leukoreduced following the removal of white blood cells or leukocytes. White blood cells can present problems for the recipient of the collected blood component by provoking immunogenic reactions. Leukoreduction may be achieved by any of the known methods in the art, including but not limited to removal of the buffy coat or filtration.

Figure 10A:
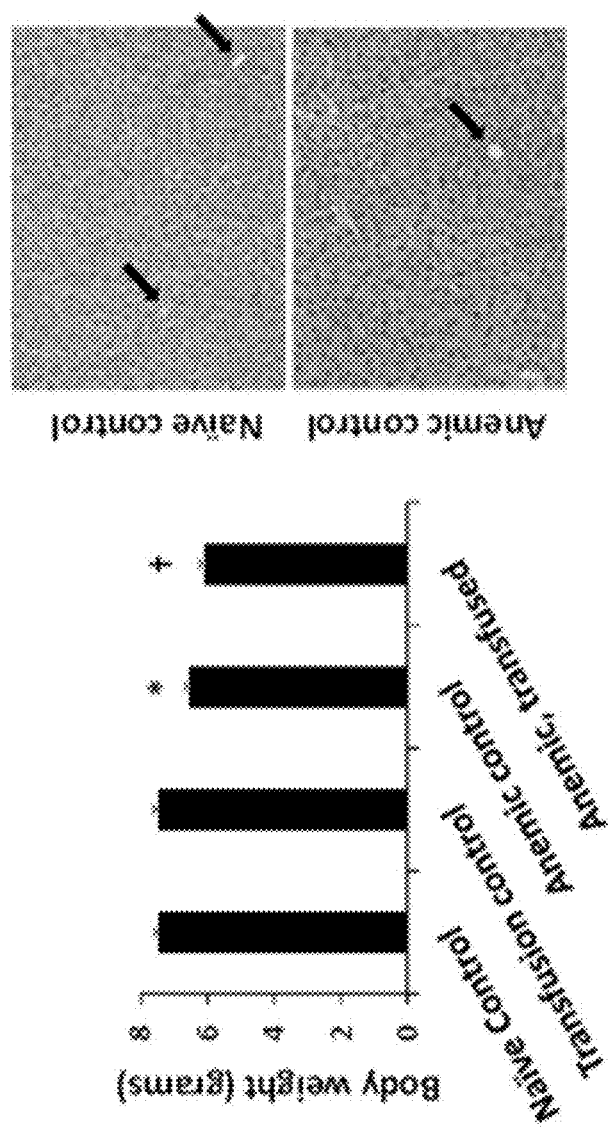
FIGS. 10A-10B show bar diagrams (means±SEM) of the body weights of mice in the 4 study groups (FIG. 10A). Photomicrographs (H&E, magnification 200×) of the liver show no evidence of venous congestion in the anemic control (FIG. 10A, solid arrows indicate central hepatic veins). Data represent 8 mice per group. Kruskal-Wallis H test, * P<0.05, † P<0.001. Differential scattergrams of RBCs being prepared for transfusions show that the removal of the buffy coat (along with some plasma and top part of the RBC layer) removed >99% of leukocytes (FIG. 10B).
Figure 10B:
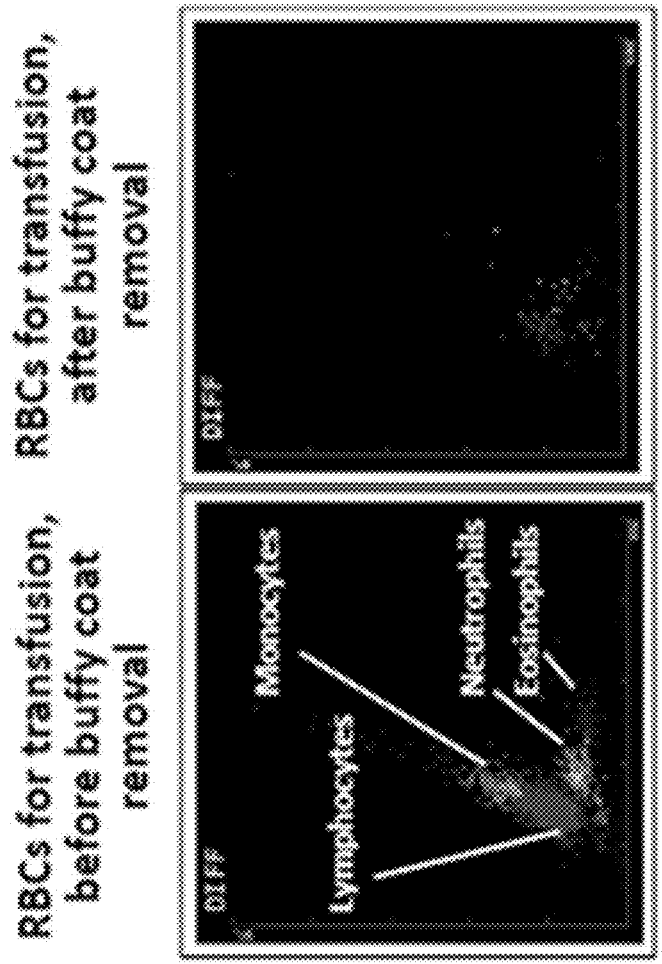

In some embodiments, the transfusion of RBCs can include between about 15 mL/kg and about 25 mL/kg of blood. In some embodiments, the transfusion of RBCs can include about 20 mL/kg of blood. In some embodiments, the transfusion is an intravenous RBC transfusion. In some embodiments, the transfusion of RBCs is collected from a donor murine animal. In some embodiments, the donor murine animal is the same murine animal. For example, the murine animal can be a C57BL mouse pup and the donor murine animal can be a C57BL adult mouse. In some embodiments, the donor murine animal is a different murine animal. For example, the murine animal can be a C57BL mouse pup and the donor murine animal can be a FVB/NJ adult mouse. For example, RBCs from adult FVB/NJ donors can be transfused into C57BL/6 recipients, which is an established model of allogeneic transfusion. Murine RBCs can be prepared for transfusion using steps similar to human blood banking, including the use of CPDA-1 anticoagulant, leukoreduction, and packing to 70% hematocrit. In some embodiments, murine RBCs can be stored for 7-14 days. In some embodiments, leukoreduction can be achieved by removing the buffy coat and not by filtration, which is the usual practice for achieving leukoreduction in human RBC units. Although the use of high-efficiency neonatal leukocyte reduction filters has been described for murine RBCs, even the smallest filters require pooled blood from 8-10 adult mice and cause at least some loss of RBC viability. To circumvent these logistical constraints, buffy coat removal was evaluated and because the results were satisfactory (FIG. 10), persisted with this method in subsequent experiments.

In some embodiments, the transfusion of RBCs can also include other components, such as buffers and the like. In some embodiments, the RBCs are washed and/or the plasma is removed prior to storage, as this may be protective of the RBCs. Washing can reduce soluble inflammatory factors such as lipids, microparticles, and cytokines, but these findings need further investigation because concerns remain about the effect of washing on RBC viability. In some embodiments, transfusion-associated NEC-like injury may not be related to antibodies present in plasma as there was no difference between allogeneic vs. syngeneic transfusions, indicating that unlike transfusion-related acute lung injury. In some embodiments, the severity of NEC-like injury can be to be higher in mice that received more than multiple RBC transfusions.

In one embodiment, the administration of at least one transfusion of red blood cells restores or increases the hematocrit levels in the murine animal to equal to or greater than 30%. In some embodiments, the hematocrit levels of the mice after the at least one transfusion of red blood cell may be equal to or greater than 30%, equal to or greater than 35%, equal to or greater than 40%, equal to or greater than 45% or equal to or greater than 50%. In some embodiments the hematocrit may be between about 30 and about 35%, between about 35 and about 40%, between about 40 and about 45%, or between about 45 and about 50%

In some embodiments, the anemic murine animal can have a hematocrit equal to or greater than 30% after the at least one transfusion of red blood cells. In some embodiments, the anemic murine animal can have a hematocrit between about 30 and about 35%, between about 35 and about 40%, between about 40 and about 45%, or between about 45 and about 50% after the at least one transfusion of red blood cells. In some embodiments, the anemic murine animal can have a hematocrit equal to or greater than 30%, equal to or greater than 35%, equal to or greater than 40%, equal to or greater than 45%, or equal to or greater than 50% after the at least one transfusion of red blood cells.

c. Gut Bacteria

Certain embodiments of the methods disclosed herein include introducing gut bacteria to the anemic murine animal prior to administering the at least one transfusion of red blood cells. In some embodiments, the gut bacteria may be introduced between postnatal day five and ten. In some embodiments, the gut bacteria may be introduced on postnatal day five, six, seven, eight, nine or ten. In some embodiments, the gut bacteria may be bacteria isolated from a human infant with neonatal NEC or adult cecal bacteria. In some embodiments, the gut bacteria may be from the class of gammaproteobacteria including but not limited to, Enterobacteriaceae, Vibrionaceae, and Pseudomonadaceae. In some embodiments, the gut bacteria may be from the genus *Serratia*.

4. Methods for Use of Murine Model of NEC

One embodiment of the present invention is a method to measure transfusion effects on anemia. For examples, such methods can be used to evaluate transfusion thresholds for premature infants, and determine if, in an expectant approach to anemia of prematurity, infants may be allowed to become far too anemic and increasing the risk of NEC when they do eventually receive a transfusion. The method includes inducing anemia in a murine animal to generate an anemic murine animal and administering at least one transfusion of red blood cells to the anemic murine animal, whereby the murine animal exhibits at least one symptom of neonatal necrotizing enterocolitis. The method includes measuring at least one of inflammatory markers or cytokines, intestinal mucosa or epithelia inflammation, macrophage infiltration of intestinal mucosa, intestinal mucosal lesions, intestinal coagulation necrosis, intestinal interstitial hemorrhages, intestinal crypt villus disruption, focal intestinal epithelia disruption, other bowel injury, or combinations thereof, before and after the transfusion of red blood cells, thereby measuring the effects of transfusion on anemia.

A particularly useful application for the murine NEC model of the invention will be in screening candidate agents for the prevention of neonatal NEC. One embodiment of the present invention provides a method for identifying and isolating an agent useful for prevention of neonatal NEC. The method includes inducing anemia in a red blood cell to generate an anemic murine animal and administering a candidate agent to the anemic murine animal thereby generating a treated anemic murine animal, and administering at least one transfusion of red blood cells to the treated anemic murine animal, whereby the treated anemic murine animal exhibits at least one symptom of neonatal necrotizing enterocolitis. The method further includes measuring at least one neonatal necrotizing enterocolitis symptom in the treated anemic murine animal and identifying the candidate agent as useful when the at least one neonatal necrotizing enterocolitis symptom in the treated anemic murine animal is improved or delayed in the treated anemic murine animal, as compared to an untreated anemic murine animal that has been administered a transfusion of red blood cells. The neonatal necrotizing enterocolitis symptom may be intestinal mucosa or epithelia inflammation, macrophage infiltration of intestinal mucosa, intestinal mucosal lesions, intestinal coagulation necrosis, intestinal interstitial hemorrhages, intestinal crypt villus disruption, focal intestinal epithelia disruption, other bowel injury, or combinations thereof.

Another particularly useful application of the murine neonatal NEC model will be in identification of agents for treating neonatal NEC, since the neonatal NEC disease in mice displays similar manifestations, severity of disease symptoms, and time of onset as NEC in human infants. One embodiment of the present invention provides a method for identifying an agent for treating neonatal necrotizing enterocolitis. The method includes administering a candidate agent to a murine animal exhibiting symptoms of neonatal NEC, such as the murine animal described herein, measuring at least one symptom of neonatal necrotizing enterocolitis symptoms before and after the candidate agent is administered to the murine animal, wherein the at least one symptom of neonatal necrotizing enterocolitis symptoms comprises intestinal mucosa or epithelia inflammation, macrophage infiltration of intestinal mucosa, intestinal mucosal lesions, intestinal coagulation necrosis, intestinal interstitial hemorrhages, intestinal crypt villus disruption, focal intestinal epithelia disruption, other bowel injury, or combinations thereof; and identifying the candidate agent as useful for treating neonatal necrotizing enterocolitis when there is an improvement in the neonatal necrotizing enterocolitis symptom after the candidate agent is administered to the murine animal. In some embodiments, the improvement in any of the neonatal necrotizing enterocolitis symptoms includes a decrease in at least one of inflammatory markers, cytokines, intestinal mucosa or epithelia inflammation, macrophage infiltration of intestinal mucosa, intestinal mucosal lesions, intestinal coagulation necrosis, intestinal interstitial hemorrhages, intestinal crypt villus disruption, focal intestinal epithelia disruption, other bowel injury, or combinations thereof. In some embodiments, the improvement in any of the neonatal necrotizing enterocolitis symptoms comprises an increase in at least one of inflammatory markers, cytokines, intestinal mucosa or epithelia inflammation, macrophage infiltration of intestinal mucosa, intestinal mucosal lesions, intestinal coagulation necrosis, intestinal interstitial hemorrhages, intestinal crypt villus disruption, focal intestinal epithelia disruption, other bowel injury, or combinations thereof

5. Murine Animal

In the methods provided above, the murine animal can be a mouse. In some embodiments, the mouse may be of any commonly used mouse strain including, but not limited to, BABL/c, C57BL, C57BR, AKR, FVB/NJ and DBA. In some embodiments, the mouse may be a mutant, knockout or transgenic mouse on the background of any commonly used mouse strain. In some embodiments, the mouse may be C57BL/6.

In some embodiments, mouse pups on P11-P13 can be used to study transfusion effects in the intestine. Using mice at this age allowed repeated measurements of hematological parameters and intravenous interventions. In terms of gut development, using P11-P13 mice can be appropriate because the murine intestine at birth resembles the midgestation human intestine and reaches the structural/functional maturity of the term human neonate (mucosal histoarchitecture, leukocyte populations, and expression of digestive enzymes and transporters) only by P18-21. In some embodiments, repeated, controlled phlebotomy to induce anemia can be used. In some embodiments, the baseline hematocrit of 40-50% in murine pups is comparable to human neonates, and with 5 phlebotomy sessions over 10 days, the hematocrit can drop to 20-24% to resemble convalescing premature infants with anemia of prematurity. Phlebotomy losses are a leading cause of anemia, in addition to the increased turnover of neonatal RBCs and normal postnatal hypoactivity of the bone marrow. In some embodiments, the anemic pups show normocytic, hypochromic anemia, indicating that incipient iron deficiency (from chronic blood loss) may also be a contributing factor. These hematological changes are similar to those seen in convalescing premature infants.

6. EXAMPLES

It will be readily apparent to those skilled in the art that other suitable modifications and adaptations of the methods of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples, which are merely intended only to illustrate some aspects and embodiments of the disclosure, and should not be viewed as limiting to the scope of the disclosure. The disclosures of all journal references, U.S. patents, and publications referred to herein are hereby incorporated by reference in their entireties.

The present disclosure has multiple aspects, illustrated by the following non-limiting examples.

Example 1

Methods and Materials

Experimental design: Animal studies were approved by the Institutional Animal Care and Use Committee. C57BL/6 mice pups were studied in 4 groups: (a) naïve control; (b) transfusion control; (c) anemic control; and (d) anemic-transfused mice. Naïve controls were maintained without intervention. Transfusion controls received an intravenous RBC transfusion (20 mL/kg into the retro-orbital venous plexus, injected in 2 aliquots on each side) on postnatal day 11 (P11). RBCs for transfusion were collected in a sterile fashion from adult FVB/NJ donors after sacrifice into citrate-phosphate-dextrose-adenine-1 (CPDA-1; Sigma, St. Louis, Mo.; 6 parts blood: 1 part CPDA-1). After centrifugation at 400 g×10 min, the buffy coat was removed along with some plasma and top part of the RBC layer for leukoreduction and the supernatant was reduced to achieve a hematocrit of 70% before storing at 4° C. in dark for 7-14 days. Anemic controls were subjected to facial vein phlebotomy to collect 40 µL blood on P2, P4, P6, P8, and P10. Hematocrits and RBC indices were measured at each phlebotomy and then everyday on P11-13; 5 µL blood was diluted 1:20 in Cellpak reagent (Sysmex, Kobe, Japan) and analyzed in the Sysmex XT-2000iV automated veterinary hematology analyzer. The anemic-transfused group underwent repeated phlebotomy as above and then received a transfusion on P11. The animals were observed for up to 48 hrs. If the hematocrit remained <30% on P12 or P13, the transfusions were repeated. Animals were sacrificed using $CO_2$ inhalation and cervical dislocation on P13, or earlier if they developed signs of illness. To measure gut barrier function, FITC-dextran was administered by gavage (10 kDa, 400 mg/kg) 4 hrs before sacrifice and measured the FITC fluorescence signal in plasma samples obtained just prior to sacrifice. To measure regional blood flow, 104 fluorescence-labeled microspheres were administered intravenously (15 µm, ThermoFisher, Waltham, Mass.) 1 hr before sacrifice and the fluorescence signal was measured in tissue lysates. In some experiments, mice with moderate anemia (hematocrit 25-30% achieved with 4 phlebotomies) were used. In other studies, pups were transfused on P10 instead of P11, prepared RBCs by resuspending in phosphate-buffered saline before storage, or used RBCs from adult C57BL/6 donors.

Genetically modified mice: C57BL/6-Tg(Csf1r-HBEGF/mCherry)1Mnz/J (stock #024046, Jackson Lab, Bar Harbor, Me.) and B6(Cg)-Tlr4tm1.2Karp/J (JAX stock #029015) have been previously described (K. MohanKumar et al., Trinitrobenzene Sulfonic Acid-induced Intestinal Injury in Neonatal Mice Activates Transcriptional Networks Similar to those seen in Human Necrotizing Enterocolitis. *Pediatr Res* 81, 99 (2016)). These mice were bred, genotyped, and used per vendor's guidelines.

Histopathology: Intestinal injury was graded as described previously by K. MohanKumar et al. (Gut mucosal injury in neonates is marked by macrophage infiltration in contrast to pleomorphic infiltrates in adult: evidence from an animal model. *Am J Physiol Gastrointest Liver Physiol* 303, G93 (July, 2012)). Briefly, grade 0: no injury; grade 1: mild separation of lamina propria; grade 2: moderate separation; grade 3: severe separation and/or edema in submucosa; grade 4: transmural injury. Colitis was graded as grade 0: no inflammation; grade 1: low level leukocyte infiltration seen in <10% high-power fields (HPF), and no structural changes; grade 2: moderate leukocyte infiltration in 10-25% HPF, crypt elongation, mucosal thickening, and no ulcerations; grade 3: high level leukocyte infiltration seen in 25-50% HPF, crypt elongation, infiltration beyond the mucosal layer, thickening of the bowel wall and superficial ulcerations; and grade 4: marked transmural leukocyte infiltration in >50% HPF, elongated and distorted crypts, bowel-wall thickening, and extensive ulcerations.

Immunohistochemistry: Formalin-fixed paraffin-embedded tissues were stained as described previously (K. MohanKumar et al., Smad7 Interrupts TGF-β Signaling in Intestinal Macrophages and Promotes Inflammatory Activation of these Cells during Necrotizing Enterocolitis. *Pediatr Res* 79, 951 (2016)). Briefly, after deparaffinization and antigen retrieval (EZ-AR Common solution, Biogenex, San Remon, Calif.), digestion with Proteinase K (20 µg/mL, 10 min; Promega, Madison, Wis.), and blocking×30 min (SuperBlock T20 blocking buffer, ThermoFisher), the slides were incubated overnight at 4° C. with rat anti-mouse F4/80, rabbit anti-mouse Ly6C (ThermoFisher), goat anti-ZO-1, goat anti-occludin, rabbit anti-myeloperoxidase (Santa Cruz Biotechnology, Santa Cruz, Calif.), and anti-4-HNE (Sigma, Burlington, Mass.). Secondary staining was performed with Alexa 488 or Alexa 568-conjugated antibodies×30 min (Invitrogen, San Diego, Calif.). Coverslips were mounted using a liquid mountant containing 4',6-diamidino-2-phenylindole (DAPI; Prolong Gold Antifade Mountant, ThermoFisher) and the tissues were imaged using a Leica SP2 confocal microscope.

To visualize cells in their native environment, tissues were embedded in 4% low melting-point agarose in 1× phosphate-buffered saline (PBS). Once the agarose was set, the block was sectioned with a vibratome to obtain slices of 40-100 µm thickness using a vibratome (Leica Microsystems, Buffalo, N.Y.). These slices were stained in a 24-well plate and then mounted on glass slides using a spacer and a coverslip. Imaging was done using a multiphoton Laser-scanning microscope (Olympus FV1000 MPE, Pittsburgh, Pa.).

Reverse transcriptase-quantitative polymerase chain reaction (RT-qPCR): Primers were designed using the Beacon Design software (Bio-Rad, Hercules, Calif.). A standard reverse transcriptase reaction was used and a SYBR green method to measure mRNA expression.

Mouse Fatty acid-binding protein 2 (FABP2, C-reactive protein, serum amyloid A, and Cxcl2): Plasma concentrations of these analytes were measured by enzyme immunoassay (MyBioSource, San Diego, Calif.; linear range 0.156-10 ng/mL).

Flow cytometry: Macrophages were defined by flow cytometry (BD LSRII, Franklin Lakes, N.J.). Intestinal tissue was washed with Hanks' balanced-salt solution (HBSS) containing 1 mM DTT (Sigma) to remove mucus, and then treated first with HBSS containing 1 mM EDTA (Sigma)×20 min at 37° C., and then with HBSS containing 1 mM collagenase type IV (Sigma)×2 hrs at 37° C. Cell suspension was stained using established protocols with the L-D viability dye (ThermoFisher), lineage cocktail (BioLegend, San Diego, Calif.), and antibodies against CD11b, Ly6C, F4/80, Ly6G, and Ly6B (BioLegend).

Murine intestinal macrophages: Murine intestinal macrophages were isolated by immunomagnetic separation, where these cells were first stained with phycoerythrin (PE)-conjugated anti-CD11b, anti-F4/80, and anti-Ly6C antibodies and then separated using anti-PE-conjugated ferromagnetic beads (Miltenyi Biotec, San Diego, Calif.). In some experiments, monocytes and macrophages were depleted by administering clodronate liposomes (Clodrosome, Brentwood, Tenn.). A 50 mg/kg intraperitoneal dose was used and an identical dose by enema on postnatal day 8, which depleted >80% monocytes and macrophages in 72 hrs (pre-determined optimum).

Cell-free hemoglobin and heme: Cell-free hemoglobin and heme were measured by visible spectroscopy (450-700 nm) using standard spectra for oxyHb, metHb, and heme as previously described (V. Sampath et al., The NFKB1 (g.-24519delATTG) variant is associated with necrotizing enterocolitis (NEC) in premature infants. *J Surg Res* 169, e51 (July, 2011)). For intracellular hemoglobin/heme measurements, RBCs were hemolysed in water (1:10) to obtain clear supernatants.

Nanoparticles with anti-NF-κB p65 siRNA: The p5RHH siRNA nanoparticles have been previously described (K. Namachivayam, K. MohanKumar, L. Garg, B. A. Torres, A. Maheshwari, Neonatal Mice with Necrotizing Enterocolitis-like Injury Develop Thrombocytopenia despite Increased Megakaryopoiesis. *Pediatr Res*, (Jan. 13, 2016)).

Statistical methods: Statistical analysis was performed using GraphPad Prism software, version 7.01 (GraphPad software, La Jolla, Calif.). Differences were considered significant at $p<0.05$.

Example 2

Neonatal Murine Model of RBC Transfusion-Associated NEC-Like Injury

In preliminary studies, mice showed near-absence of Gammaproteobacteria in their intestines, and therefore, *Serratia marcescens* isolated from a human infant with NEC ($10^4$ colony-forming units; gavage) was introduced in all groups on postnatal day 7 (P7) (FIG. 1A). The *Serratia* spp. was established and the final gut microbial composition in these mice then resembled premature human infants at risk of NEC.

Figure 1C:
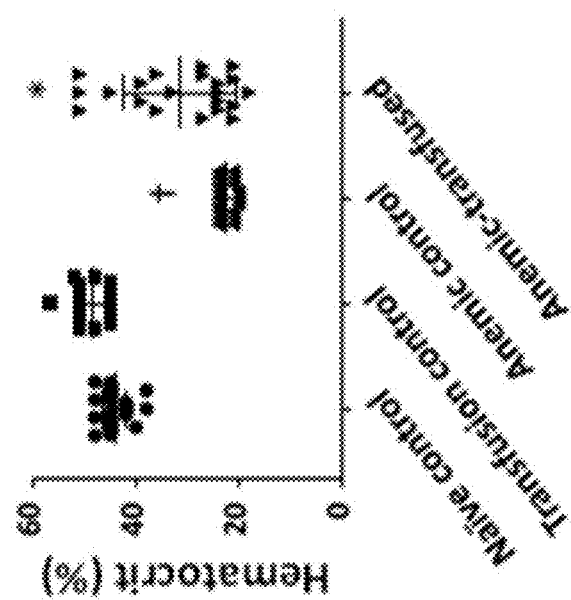
Figure 1B:
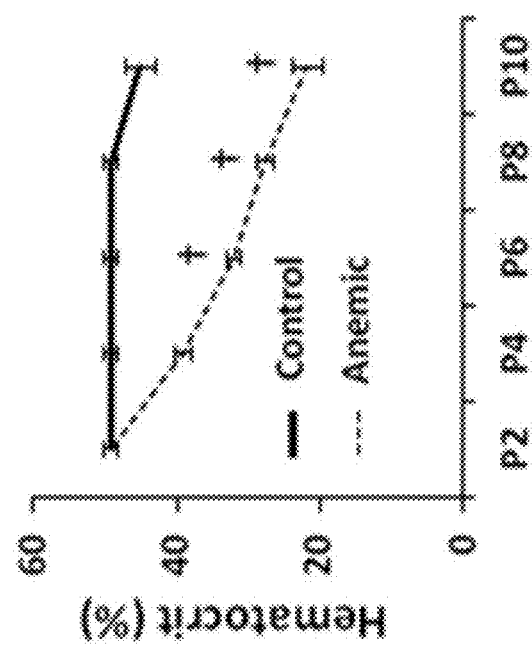

The naïve controls were observed without further intervention. The anemic control and anemic-transfused groups were rendered anemic by repeated, controlled phlebotomy on P2, P4, P6, P8, and P10. Hematocrits and RBC parameters were checked prior to each phlebotomy, and then every 24 hrs on P11, P12, and P13. In phlebotomized mice, the hematocrit dropped from 49.2±1% on P2 to 21.7±0.4% after the 5th phlebotomy on P10 (p<0.001; FIG. 1B). The anemic control and anemic-transfused pups showed normal physical activity, no weight gain, and on autopsy, no hepatic venous congestion (FIG. 10A), indicating that these animals were not likely to have developed congestive heart failure due to severe anemia.

The transfusion control and anemic-transfused groups received an allogeneic RBC transfusion on P11 with leuko-reduced, packed RBCs (20 mL/kg RBCs obtained from FVB/NJ donors, injected into the retro-orbital venous plexus). These transfused RBCs had been previously leuko-reduced by buffy coat removal to eliminate >99% leukocytes and platelets, packed to a hematocrit of 70%, and stored at 4° C. for 7 days. The hematocrits in the naïve control, transfusion control, anemic control, and the anemic-transfused groups at the time of sacrifice are depicted in FIG. 1C, and other RBCs indices are summarized in Table 1. Compared to naïve control, the anemic control group showed lower mean corpuscular hemoglobin, mean corpuscular hemoglobin concentration, and reticulocyte hemoglobin. In 8/21 (38.1%) anemic-transfused mice, the hematocrit remained <30% after the 1st transfusion, and therefore, these pups were transfused again. Animals were sacrificed on P13, or earlier if they developed physical distress.

2D) indicated a strong resemblance to human NEC. Focal epithelial disruption and inflammation was seen in all animals in this group.

Example 4

Figures 3A, 3B:
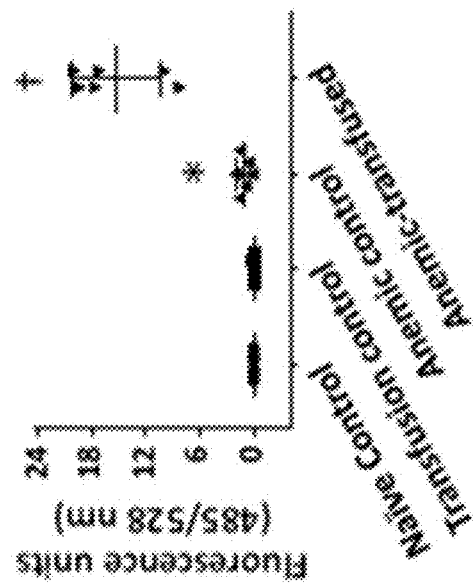
FIGS. 3A-3E show that RBC transfusion-associated NEC-like injury disrupts the epithelial barrier and is marked by a prominent inflammatory response. Scatter column plots (means±SD) show plasma FABP2 concentrations just before sacrifice (FIG. 3A) and fluorescence readings in plasma 4 hrs after gavage with FITC-dextran (FIG. 3B). Plasma CXCL2, C-reactive protein, and serum amyloid A were measured by ELISA (FIG. 3C). Scatter plots (means±SD) show the fluorescence readings, representative of seeding density of fluorescence-labeled polystyrene microspheres, in ileocecal tissue lysates (FIG. 3D), which estimates regional blood flow. The cellular inflammatory response is apparent from increases in leukocytes and macrophages in distal ileum and proximal colon in NEC-like injury (FIG. 3E). Scatter plots (means±SD) show the number of leukocytes per high-magnification field. H&E-stained photomicrograph (magnification 250×) of proximal colon from an anemic-transfused mouse pup shows numerous macrophages (arrows) in colonic tissue at the edge of an ulcer. Scale bar=100 µm; N=8 mice per group. Kruskal-Wallis H test with Dunn's post-test, * P<0.05, **

RBC Transfusion-Associated NEC-Like Injury in Mouse Model Disrupts the Epithelial Barrier and Causes Prominent Cellular Inflammatory Response Because villus disruption can occur with post-mortem/autolytic changes in the neonatal intestine, the crypt-villus disruption seen in the anemic-transfused intestine that occurred ante mortem and represented NEC-like injury was confirmed. Tissue sections were carefully screened, and found negative, for signs of autolysis such as RBC hemolysis and loss of differential staining in the layers of the bowel wall. FABP2, a cytosolic protein uniquely located in enterocytes and a sensitive biochemical marker of gut mucosal injury, was also measured in plasma samples obtained just prior to sacrifice (FIG. 3A). FABP2 levels in anemic-transfused mice were 4-fold higher than control (p<0.001).

To determine the extent of transfusion-associated bowel injury and confirm that the tissue damage was not limited to localized mucosal lesions, the gut barrier function in mice

TABLE 1

Hematocrit and red cell indices in controls and anemic-transfused pups

|  | Naïve control (N = 42) | Transfusion control (N = 21) | Anemic control (N = 40) | Anemic, transfused (N = 21) |
|---|---|---|---|---|
| Hematocrit [%; median (range)] | 45 (42-57) | 45 (33-57) | 22.5 (18-24)† | 27 (18-51)† |
| Mean corpuscular volume [fL; median (range)] | 51.9 (45.1-75.3) | 53.5 (45.9-57.8) | 51.8 (42.5-62.5) | 50 (44-58.8) |
| Mean corpuscular hemoglobin [pg; median (range)] | 15.8 (14.3-16.8) | 16 (13.8-16.8) | 14 (11-15.7)† | 14.1 (13.2-15)† |
| Mean corpuscular hemoglobin concentration [g/dL; median (range)] | 30.6 (26-32.8) | 30 (27.1-33.3) | 27.3 (24.2-33.3)** | 28.4 (23.3-31.2) |
| Red cell distribution width [fL; median (range)] | 35.6 (26.9-48.5) | 32.9 (28.6-37.1)† | 38 (32.5-49.3) | 33.2 (26.4-52.9) |

**P < 0.01,
†P < 0.001.

Example 3

Figure 2C:
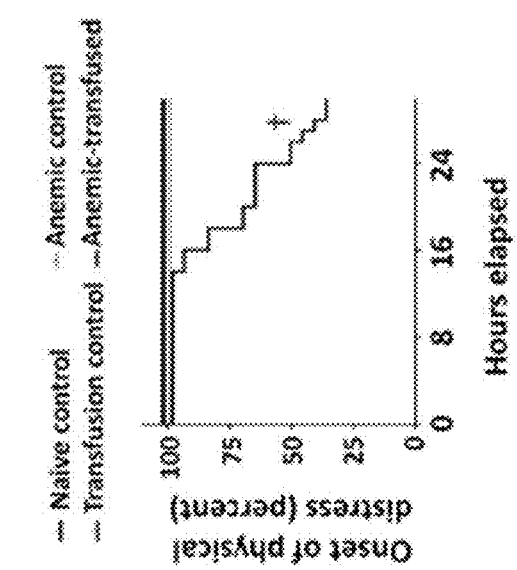
FIGS. 2A-2D show that RBC transfusions trigger NEC-like injury in neonatal mice with severe anemia. Photographs show hemorrhagic injury in ileocecal and mid-colonic regions (FIG. 2A, arrows) in anemic-transfused animals. The naïve control, transfusion control, and anemic control groups did not develop bowel injury. A composite bar chart (FIG. 2B) shows the frequency of NEC-like injury occurrence in the anemic-transfused mice; Fisher's exact test, † P<0.001. Kaplan-Meier curves (FIG. 2C) show the onset of NEC-like injury in anemic-transfused mice; Mantel-Cox log-rank test, † P<0.001. Representative photomicrographs (hematoxylin-eosin; magnification 250×) of the ileum (FIG. 2D, left) and the colon (FIG. 2D, right) show NEC-like injury in anemic-transfused mice. Scale bars=100 µm. Scatter column plots (means±standard deviation) summarize the severity of bowel injury. N=42 in naïve control, 21 in transfusion control, 18 in anemic control, and 21 in the anemic-transfused group. Kruskal-Wallis H test with Dunn's post-test, † (dagger) P<0.001 vs. naïve control.
Figure 2B:
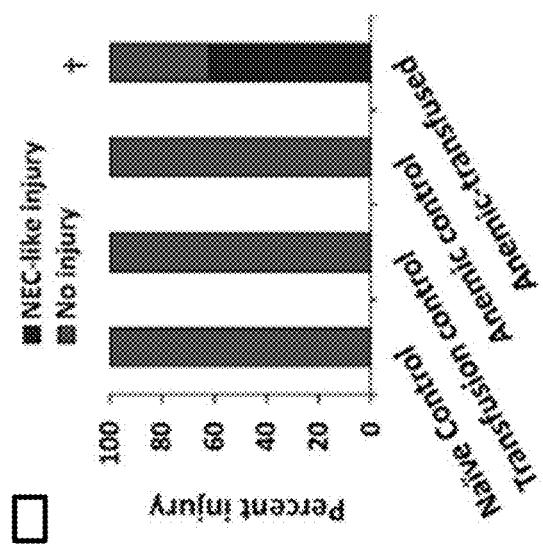
Figure 2A:
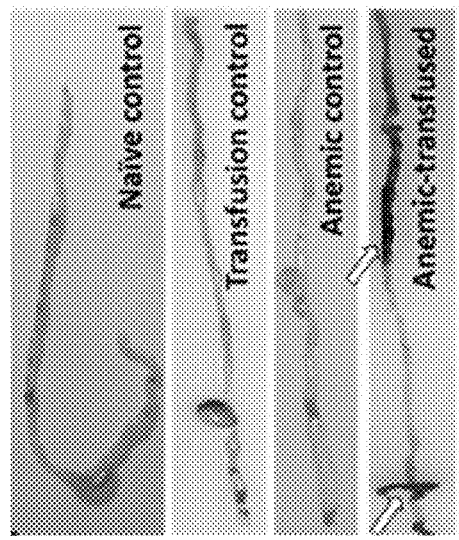
Figure 2D:
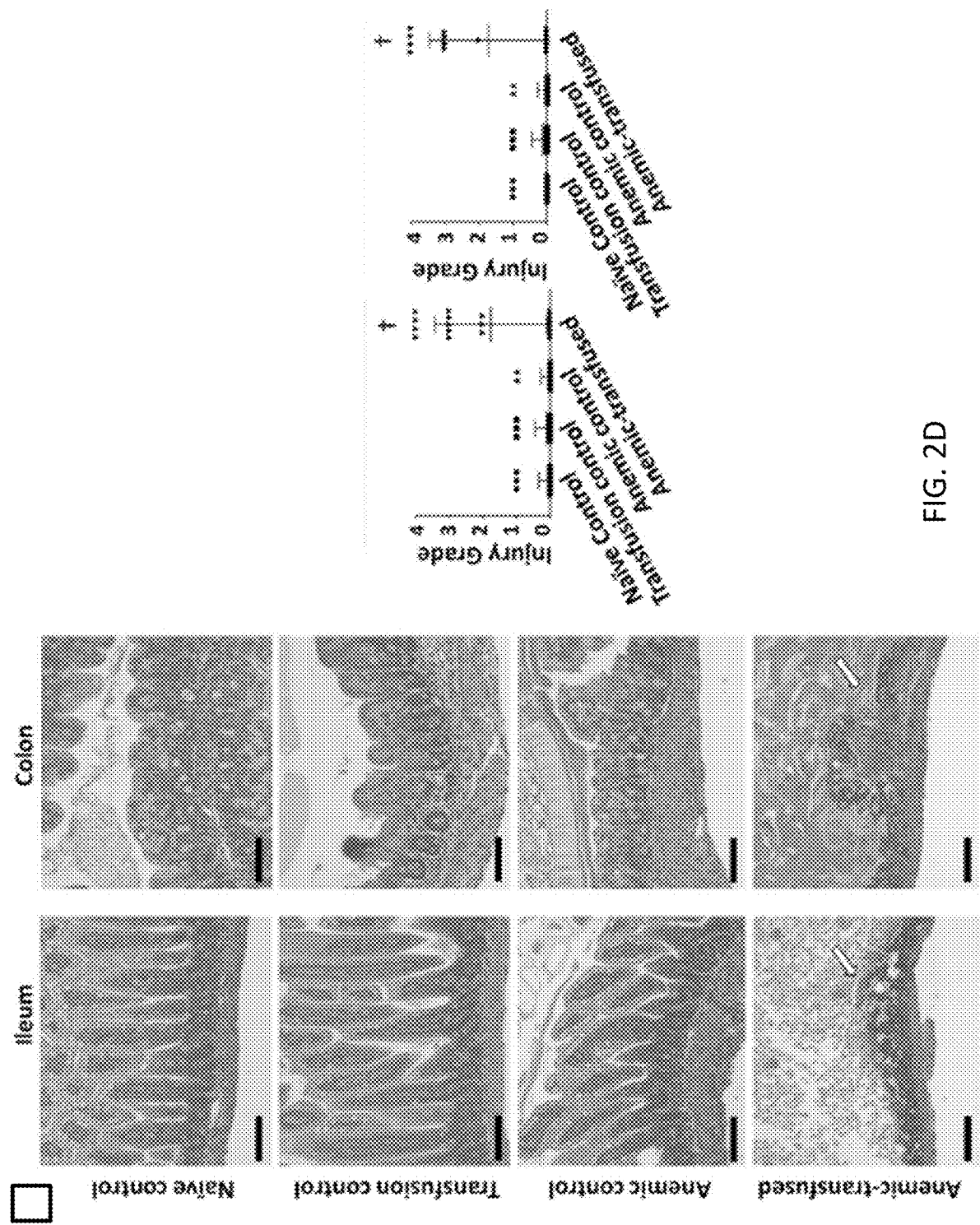

RBC Transfusions Trigger NEC-Like Injury in Neonatal Mouse Model with Severe Anemia Intestinal injury was seen only in anemic-transfused mice. RBC transfusions caused no harm in the transfusion control group. Mucosal injury was graded on an established, 4-point scale of NEC-like injury. Thirteen of the 21 mice (61.9%) in the anemic-transfused group developed NEC-like injury involving the ileocecal and mid-colonic regions; these 13 mice showed mucosal injury ≥grade 2 in the ileocecal and the mid-colonic regions at 18-28 hrs after RBC transfusions (FIGS. 2A-2C). Histopathological findings of coagulation necrosis, inflammation, and interstitial hemorrhages (FIG.

was evaluated using an established protocol (S. R. Shiou et al., Erythropoietin protects intestinal epithelial barrier function and lowers the incidence of experimental neonatal necrotizing enterocolitis. The Journal of Biological Chemistry 286, 12123 (Apr. 8, 2011)). FITC-dextran was administered by gavage 4 hrs prior to sacrifice in all 4 groups and the fluorescence signal of FITC was measured in plasma just prior to sacrifice. There was a small, albeit statistically-significant increase in gut mucosal permeability in anemic mice. The anemic-transfused group showed a marked increase in the plasma fluorescence readings (FIG. 3B; p<0.001), even in mice without remarkable gross/histopathological evidence of bowel injury. Consistent with these data, the anemic and anemic-transfused intestine also showed decreased epithelial immunoreactivity for the tight junction proteins, zonula occludens-1 (ZO-1) and occludin.

Figure 3C:
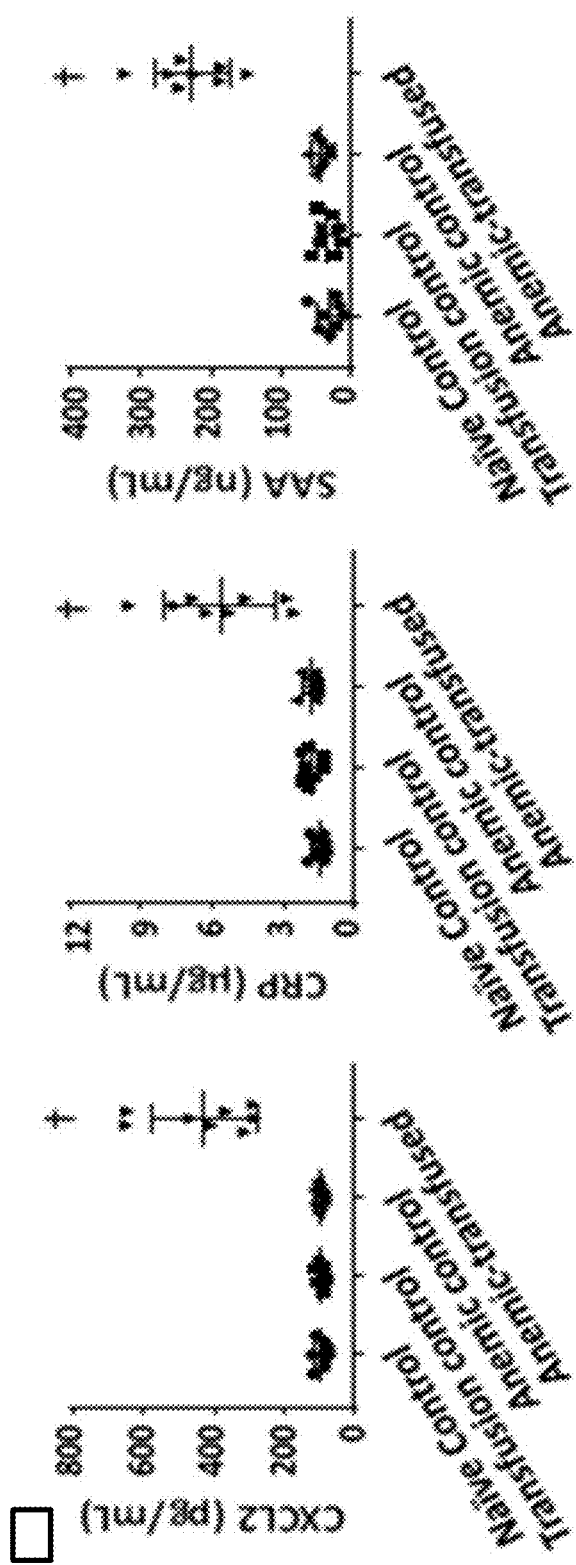

Seeking further evidence that the bowel injury in the anemic-transfused mice resembled human NEC, plasma concentrations of CXC-motif ligand 2 (Cxcl2), C-reactive protein, and serum amyloid A, three inflammatory markers that are consistently increased in human NEC were measured. Compared to the control groups, the anemic-transfused mice showed elevated levels of all 3 analytes (FIG. 3C).

To investigate the mechanism(s) by which transfusions caused NEC-like injury, the ability of transfused RBCs to impair intestinal perfusion and cause ischemic injury in a background of severe anemia, which presumably could have caused tissue hypoxia, was tested. To evaluate regional blood flow, fluorescence-labeled polystyrene microspheres were administered intravenously 1 hr prior to sacrifice (schematic in FIG. 1A).

Figure 3E:
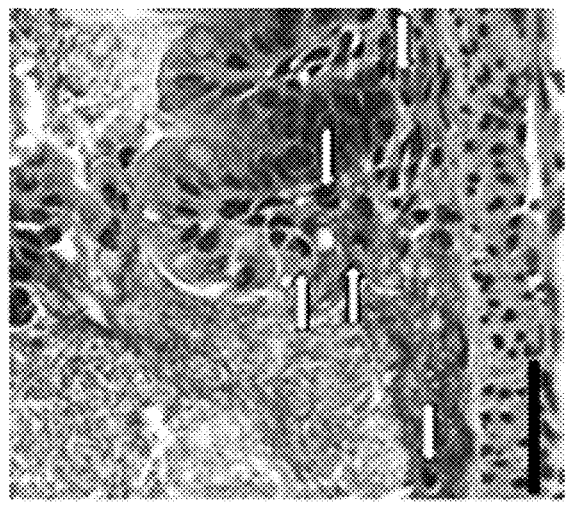
Figure 3D:
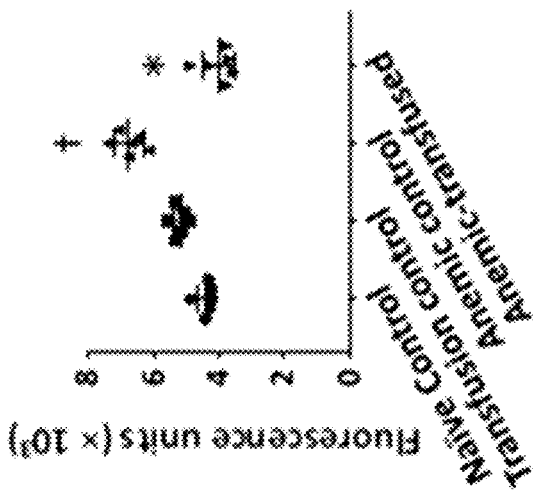

These microspheres get lodged in capillaries, and the seeding density in tissues provides an indirect, but reliable estimate of regional perfusion. The focus was on the ileocecal area, which was affected in the anemic-transfused mice and is also frequently involved in human NEC. Compared to naïve control, the transfusion control and anemic groups showed increased microsphere seeding in ileocecal tissue. In anemic-transfused mice, the microsphere seeding was comparable to the naïve controls (FIG. 3D). Similar, but somewhat less pronounced, changes in microsphere seeding were seen in other intestinal regions. In absence of convincing evidence for bowel ischemia following transfusions either in control or the anemic-transfused groups, inflammation as an alternative mechanism of bowel injury was questioned. The anemic-transfused intestine showed increased cellularity in NEC-like lesions, and many infiltrating cells showed a macrophage-like appearance (abundant cytoplasm, eccentrically-placed reniform nucleus; FIG. 3E).

Example 5

Macrophage Infiltration in RBC Transfusion-Associated NEC-Like Injury in Mouse Model To define the cellular inflammatory response during transfusion-associated bowel injury, flow cytometry was used to examine cell suspensions from enzymatically-digested tissue samples. To differentiate inflammatory monocytes from neutrophils, CD11b+ myeloid cells were gated on macrophage markers. In naïve control and the transfusion control intestine, the CD11b+ fraction was comprised of F4/80$^{hi}$ macrophages (FIG. 4A) that expressed CD115 and included Ly6C$^{lo}$ and Ly6C$^{hi}$ cells (FIG. 4B). These phenotypic features were consistent with those of a maturing population of resident macrophages.

In anemic control and the anemic-transfused intestine, the CD11b+ fraction was enriched (FIG. 4A). In addition to the F4/80$^{hi}$ resident macrophages, a sizable F4/80$^{mid}$ population was also seen. These F4/80$^{mid}$ cells showed a CD115+ Ly6C$^{hi}$ phenotype characteristic of 'inflammatory' macrophages derived from newly-recruited blood monocytes (FIG. 4B). Similar macrophage infiltration was found in the intestines of anemic TLR4-null mice, indicating that the mucosal inflammatory response during anemia was not dependent on specific Gram-negative bacteria or their products. The F4/80$^{low}$ population was comprised of CD115+ Ly6C$^{lo}$ macrophages derived from non-classical monocytes and some neutrophils, including a small population of mature Ly6G$^{hi}$ Ly6B+ neutrophils and a few Ly6G$^{mid}$ Ly6B+ late-lineage neutrophil precursors (FIG. 4C).

Figure 4D:
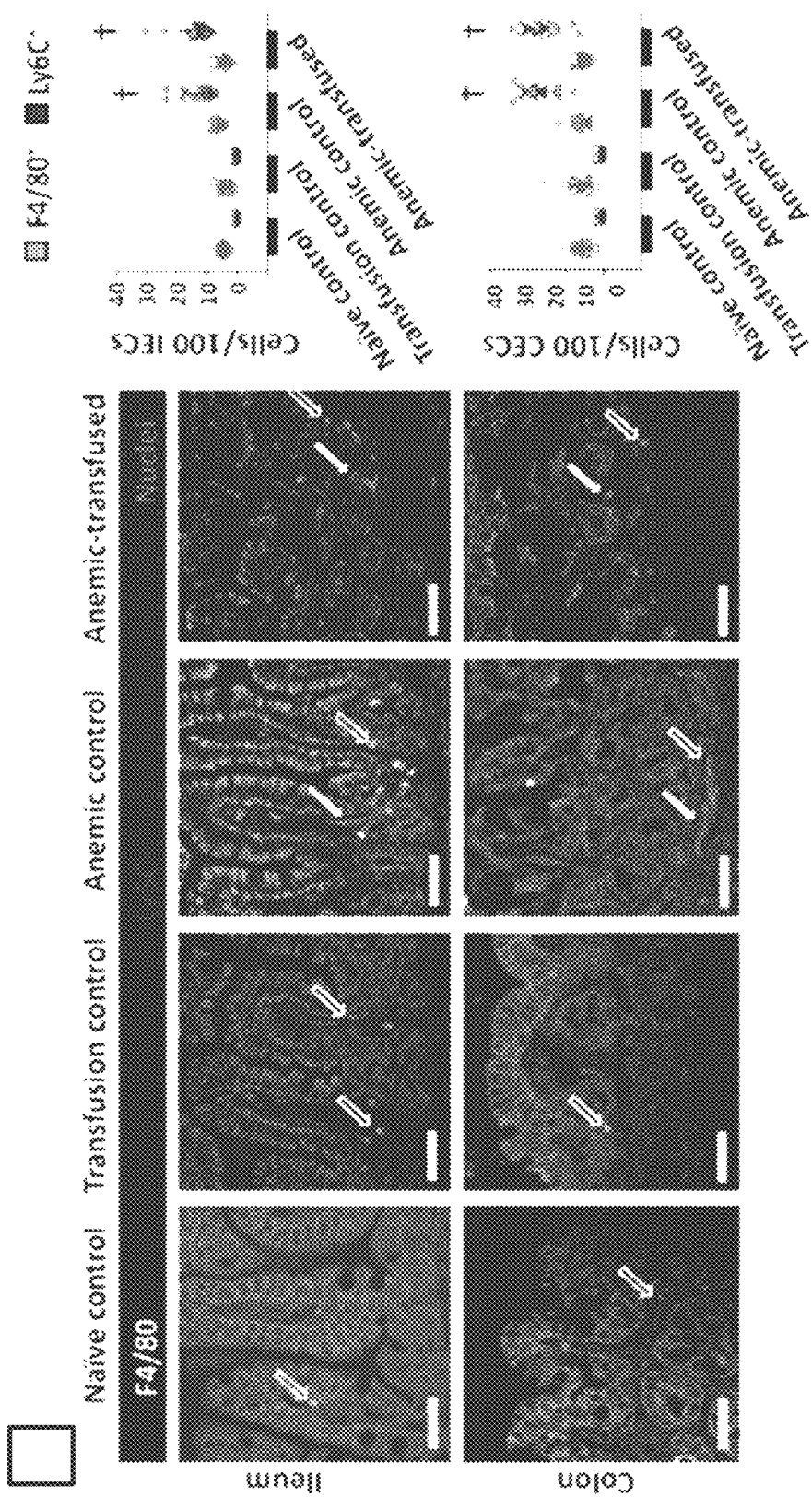

Immunofluorescence microscopy showed Ly6C+ macrophages in comparable numbers in the anemic control and the anemic-transfused intestine. These findings contrasted with the naïve and transfusion controls, which showed only scattered F4/80+ macrophages with no/minimal staining for Ly6C (FIG. 4D).

Example 6

Figures 5A, 5B:
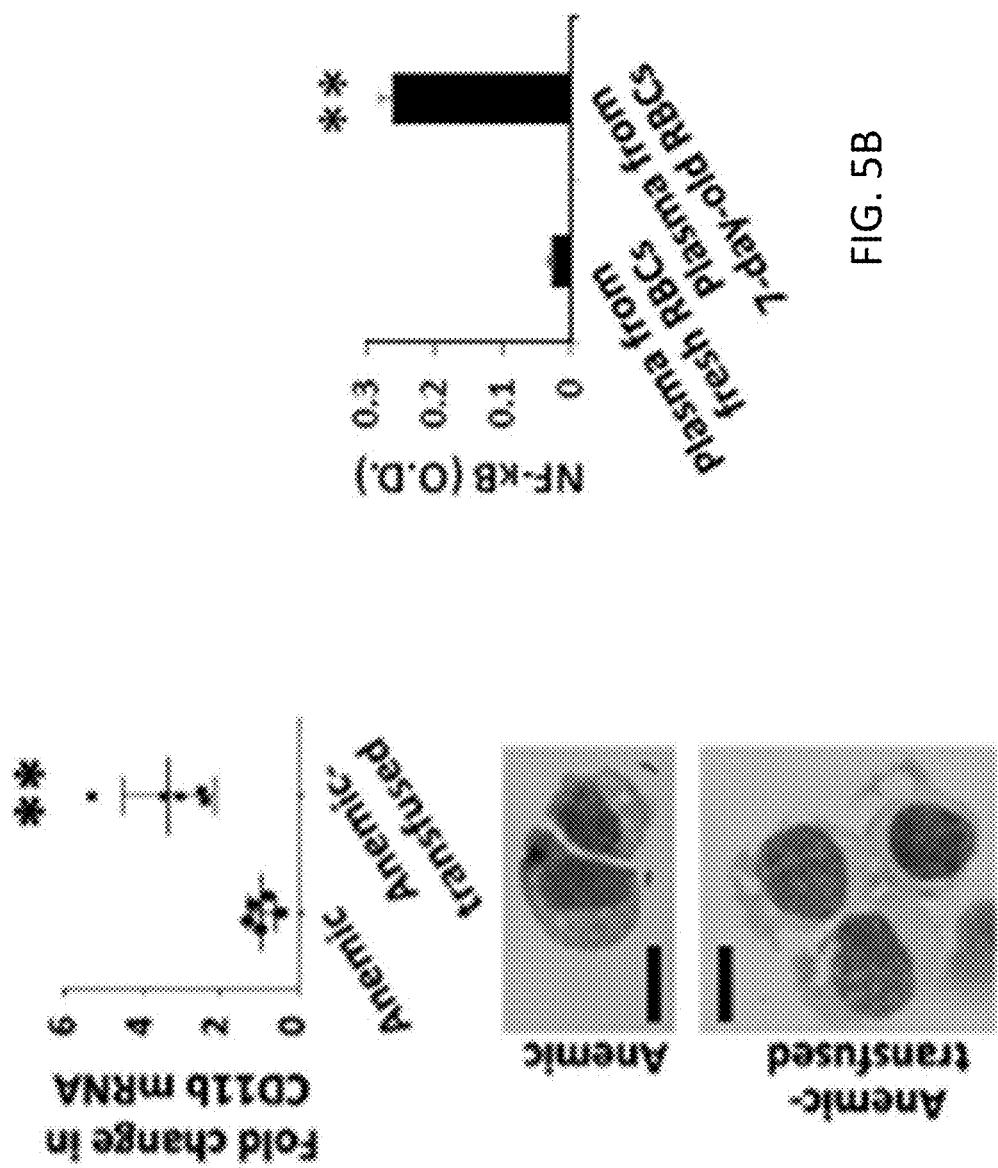
FIGS. 5A-5J show that RBC transfusions activated leukocytes present in the anemic intestine. Photomicrographs (FIG. 5A) show 'activated' morphology of macrophages from the anemic-transfused intestine. Wright-Giemsa stain, magnification 1000×. Scale bar 5 µm. A scatter plot (means±SD) shows increased CD11b mRNA expression in macrophages from anemic-transfused intestine vs. anemic control (FIG. 5A). Data normalized against 18S rRNA; Mann-Whitney U test,  P<0.01. A bar diagram (mean±SEM) shows relative NF-κB activity (optical density for secreted embryonic alkaline phosphatase activity) in NF-κB/SEAP reporter cells treated with plasma from RBCs that had been freshly-isolated from adult donors, vs. plasma from RBCs that had been storage for 7 days (FIG. 5B). Data represent three experiments; Mann-Whitney U test,  P<0.01. Fluorescence photomicrographs (magnification 400×) of anemic control and anemic-transfused intestine show immunoreactivity for Ly6C (FIG. 5C, filled triangles) and 4-hydroxynonenal (FIG. 5C, 4-HNE, open triangles). Ly6C+ macrophages in anemic-transfused intestine expressed 4-HNE (FIG. 5C, solid arrows), but not in the anemic control (FIG. 5C, open arrows). 4-HNE was also detected in nearby epithelium. Scale bar 50 µm. Some neutrophils also showed extracellular trap formation (FIG. 5D, open arrow) and 3D image reconstruction traces show the course of the neutrophil extracellular trap (FIG. 5D (right hand box), open arrow). Scatter plots (means±SD) show the severity of NEC-like injury following allogeneic (FVB/NJ donors) vs. syngeneic (C57BL/6 donors) RBC transfusions (FIG. 5E). N=18 mice/group. Scatter plots (means±SD) also show relative NF-κB activity (optical density) in NF-κB reporter RAW264.7 macrophages treated with fresh leuko-reduced RBCs (control), 7-day-stored RBCs, fresh RBCs resuspended in PBS, 7-day RBCs stored in PBS, plasma supernatant from fresh and 7-day RBCs, fresh RBCs mixed with supernatant from 7-day-stored transfusion units, and 7-day RBCs mixed with fresh plasma (FIG. 5F). Data represents 4 different donors, each with 2 technical replicates; Kruskal-Wallis H test with Dunn's post-test, * P<0.05, ** P<0.01, † P<0.001 vs. control. Scatter plots (means±SD) show oxyHb, metHb, and heme concentrations in RBC fractions and plasma supernatants from 7-day-stored FVB/NJ RBCs (FIG. 5G). N=6 donors. Scatter plots (means±SD) show relative NF-κB activity in reporter macrophages treated with hemin (10 µM), 7-day RBCs, or 7-day RBCs along with haptoglobin (10 µg/mL) (FIG. 5H). N=8 donors. † P<0.001 vs. 7-day-stored RBCs, Mann-Whitney U test. Kaplan-Meier curves show onset of NEC-like injury in anemic and anemic-transfused mice treated with intravenous haptoglobin 10 µg/g body weight 1 hr before transfusion (FIG. 5I). 1 haptoglobin-treated mouse died 2 hrs after procedure and was excluded; Mantel-Cox log-rank test, * P<0.05. Scatter column plots (means±SD) summarize the severity of bowel injury (FIG. 5J). N=5 anemic control, 4 anemic control treated with haptoglobin, 8 each in anemic-transfused and anemic-transfused treated with haptoglobin; Kruskal-Wallis H test with Dunn's post-test, * P<0.05, ** P<0.05 vs. anemic control, # P<0.05 vs anemic treated with haptoglobin, and ζ P<0.05 vs anemic-transfused.

RBC Transfusions Activated Leukocytes Present in the Anemic Intestine in Mouse Model The anemic intestine contained nearly as many F4/80mid Ly6Chi macrophages as the anemic-transfused intestine, but bowel injury was seen only in the latter. Therefore, the ability of RBC transfusions to activate the macrophages present in the anemic intestine was questioned. Ly6C+ cells were isolated from the anemic control and the anemic-transfused intestine by immunomagnetic sorting and CD11b expression was compared by reverse transcriptase-quantitative polymerase chain reaction (RT-qPCR). Consistent with the hypothesis, there was a 3-fold increase in CD11b expression in macrophages from the anemic-transfused intestine over anemic control (FIG. 5A). Macrophages from the anemic-transfused intestine showed an 'activated' appearance with cytoskeletal changes such as increased ruffling and pseudopodia formation (FIG. 5A). A NF-κB/SEAP reporter RAW264.7 cell line (Imgenex, San Diego, Calif.), which shows NF-κB-driven expression of secreted embryonic alkaline phosphatase, was treated with plasma from freshly-harvested adult RBCs before storage vs. plasma from 7-day-stored RBCs. As shown in FIG. 5B, plasma from stored RBCs activated NF-κB signaling in the macrophage-like reporter cells.

Figure 5C:
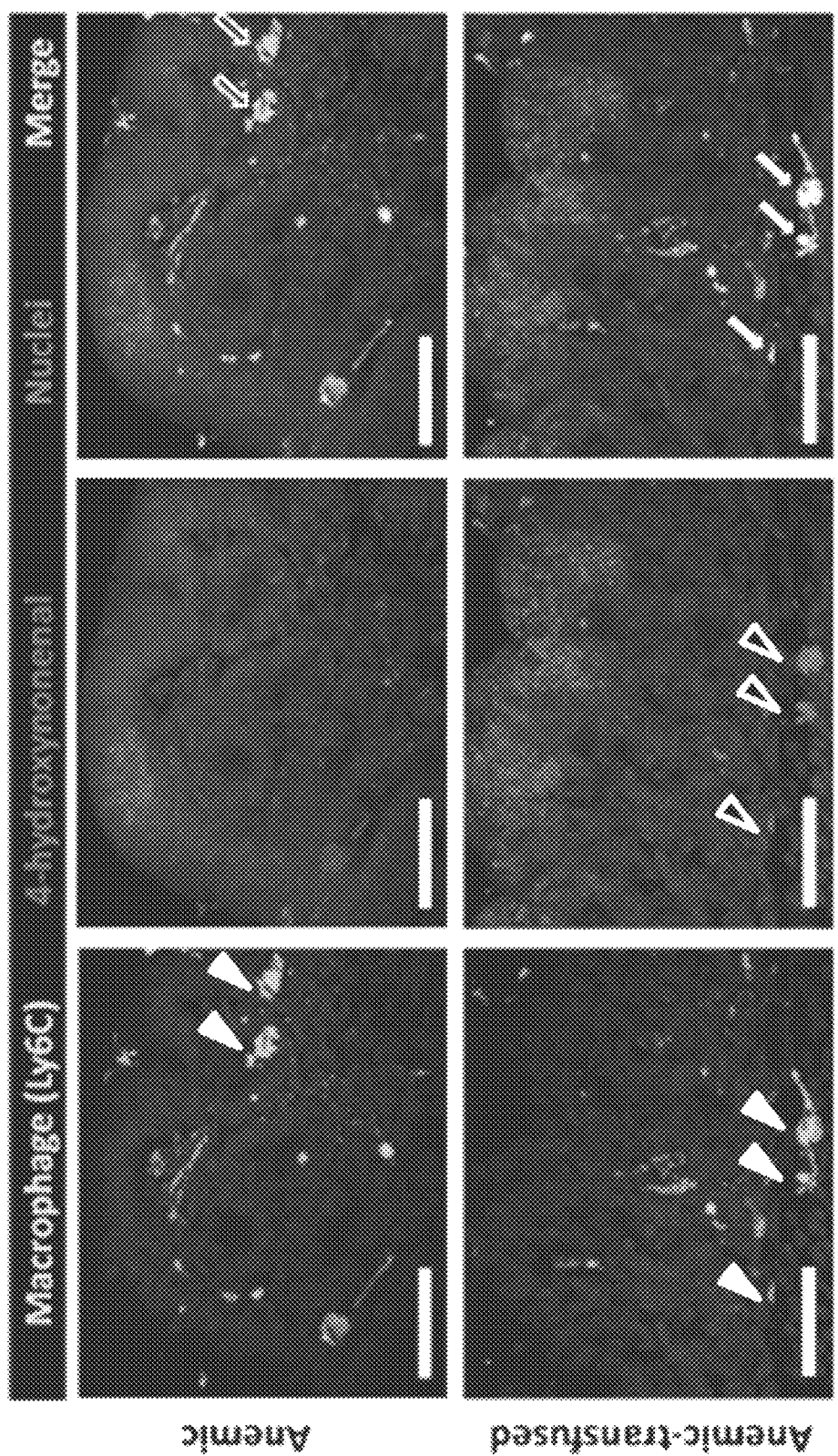
Figure 5D:
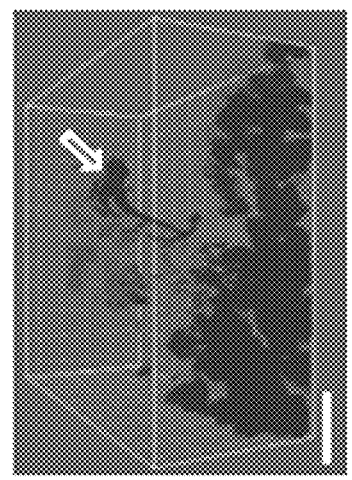
Figure 5D:
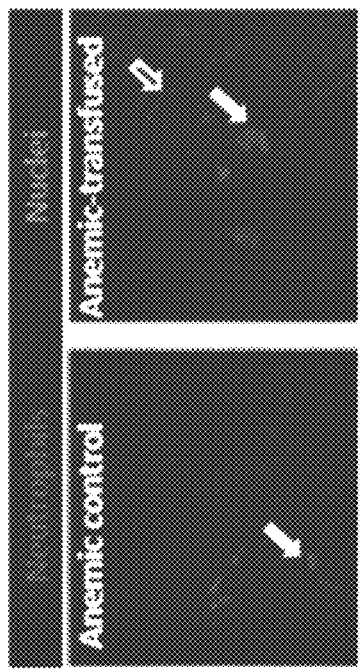

To further define the activated state, macrophages in the anemic control vs. the anemic-transfused intestine were compared for evidence of generation of reactive oxygen species (ROS). Macrophages in the anemic-transfused, but not in the anemic control intestine, showed 4-hydroxynonenal (4-HNE), which is a product of membrane lipid peroxidation. 4-HNE was also detectable in the epithelium in close vicinity of these macrophages (FIG. 5C) and in the few neutrophils present in the mucosa (not depicted. Some neutrophils in the anemic-transfused intestine showed extracellular trap formation (FIG. 5D), indicating that the inflammatory effects of RBC transfusions were not specific for macrophages and may have activated all leukocytes present in the anemic intestine.

Figure 5F:
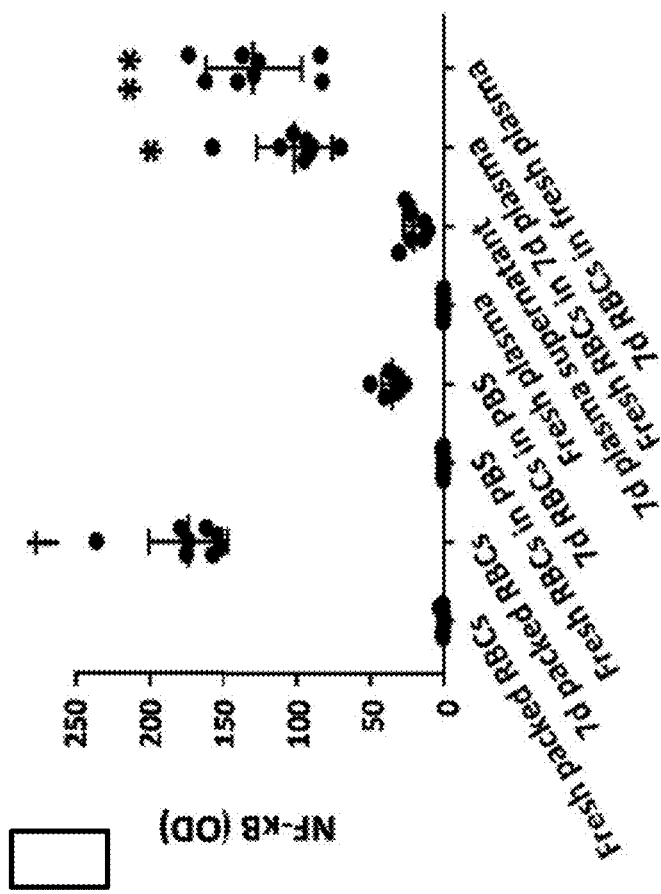
Figure 5E:
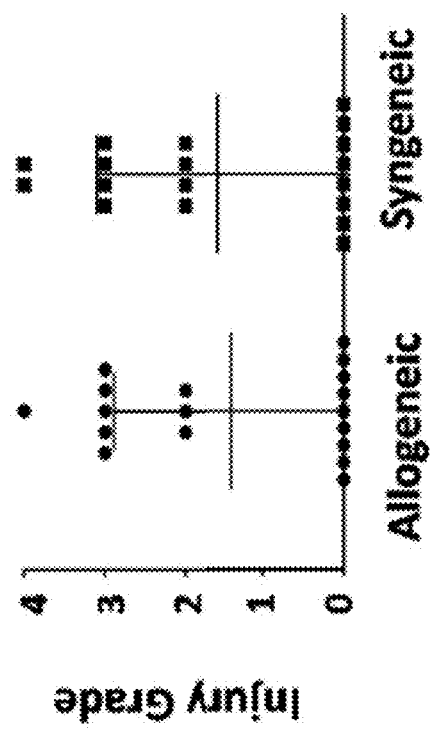

To determine the mechanism by which RBC transfusions activated gut macrophages, allogeneic (FVB donors) vs. syngeneic (C57BL/6 donors) transfusions were compared but no difference between the two groups was found (FIG. 5E). To ascertain the contribution of the RBC fraction vs. the plasma supernatants in transfused RBCs towards macrophage activation, a nuclear factor-kappa B (NF-κB) reporter murine RAW264.7 macrophage cell line was used (Imgenex, San Diego, Calif.). Using freshly-isolated, leukoreduced RBCs as control, 7-day-stored RBCs (typically used for transfusions), separated RBC or plasma fractions, freshly-isolated RBC fraction mixed with plasma from 7-day RBCs, were compared to 7-day RBCs mixed with freshly-isolated plasma (FIG. 5F). Storage of RBC units increased the inflammatory potential of the transfused RBCs and the constituent RBC or plasma fractions. Interestingly, freshly-isolated RBCs suspended in plasma fraction from 7-day-stored transfusion units, or 7-day RBCs suspended in fresh plasma had a similar inflammatory effect. These data suggested that the inflammatory effects of transfused RBCs were caused by factors released from aging RBCs such as free hemoglobin and/or heme.

Figure 5H:
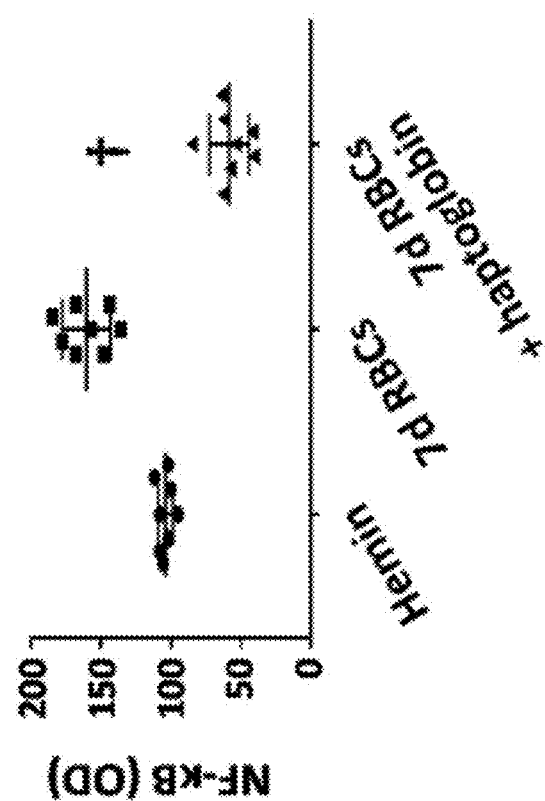
Figure 5G:
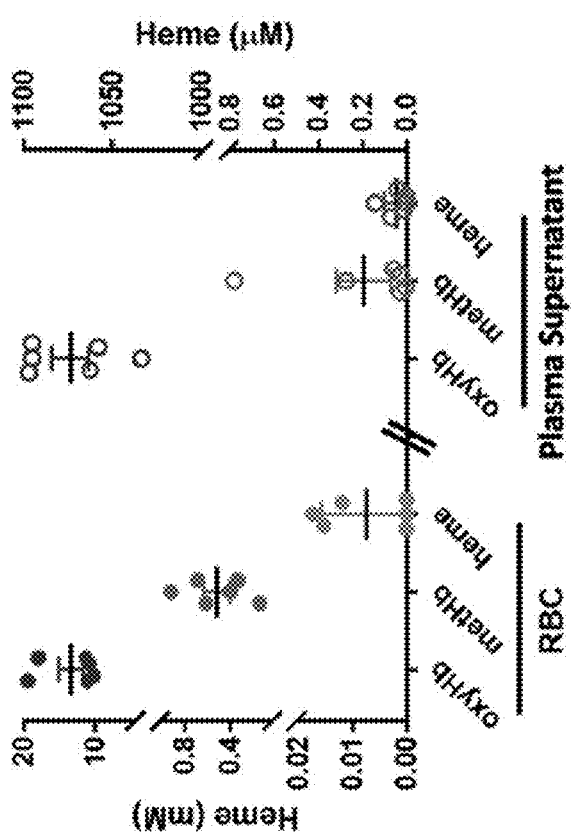

Oxyhemoglobin (oxyHb), methemoglobin (metHb) and heme in the packed RBC fraction and the plasma supernatants from 7-day RBC transfusion units were measured. Cell-free oxyHb levels were consistently elevated in all transfusion units (FIG. 5G). In support of a possible role of free hemoglobin, the inflammatory effect of 7-day-stored RBC units on macrophages was reversed by adding recombinant haptoglobin, which is a natural chelator of free hemoglobin (FIG. 5H). These findings were of interest because human neonates have very low plasma haptoglobin levels, and mouse pups also showed significantly lower plasma haptoglobin than adult mice. Therefore, recombinant haptoglobin was administered intravenously in some anemic-transfused pups, 1 hr prior to transfusion.

Figure 5J:
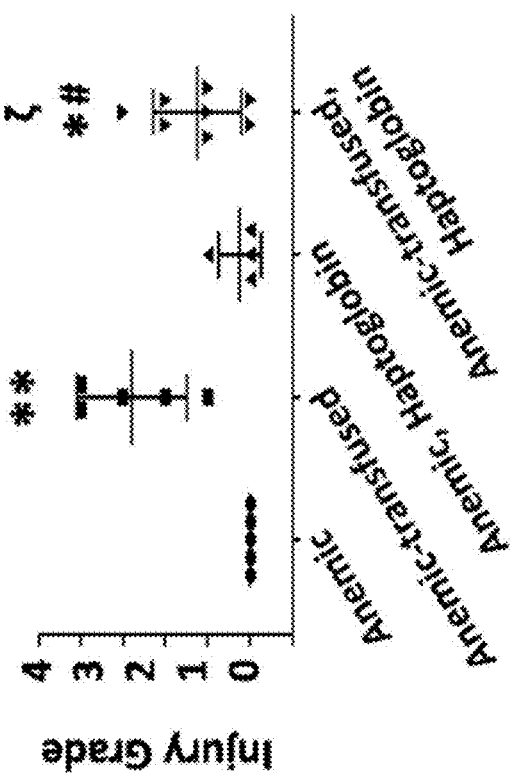
Figure 5I:
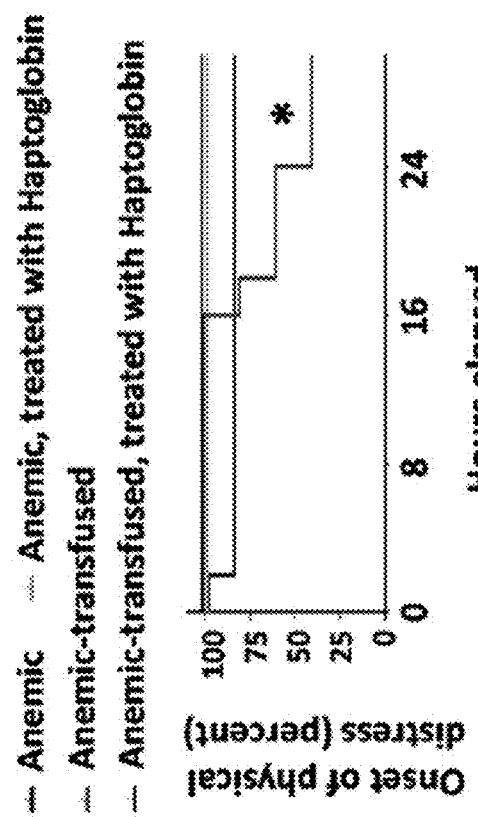

Haptoglobin pre-treatment was protective (FIGS. 5I-5J). Consistent with existing information that the inflammatory effects of cell-free hemoglobin are mediated via TLR4, TLR4-null mice were found to be protected from transfusion-associated injury.

Example 7

Figure 6A:
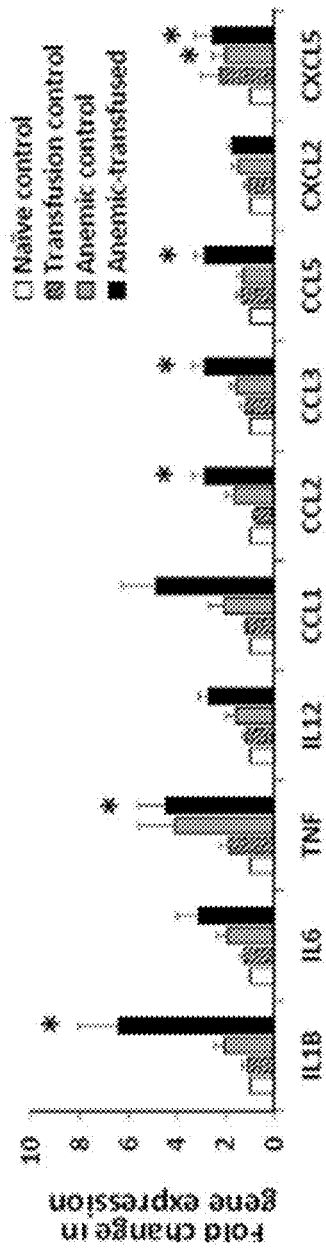
FIGS. 6A-6C show that transfusion-associated NEC-like injury induced the expression of various inflammatory genes. Bar diagrams (means±SEM) show the fold change in mRNA expression in tissue samples obtained from control and anemic-transfused mice.
Figure 6B:
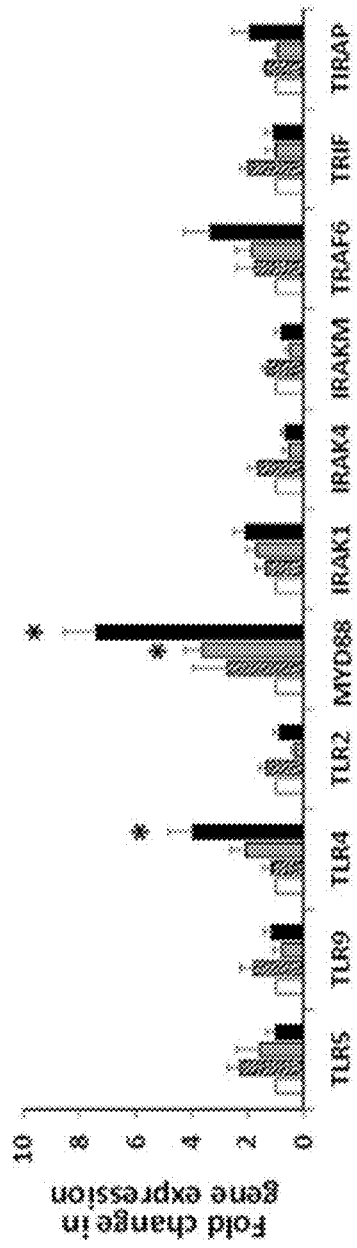
Figure 6C:
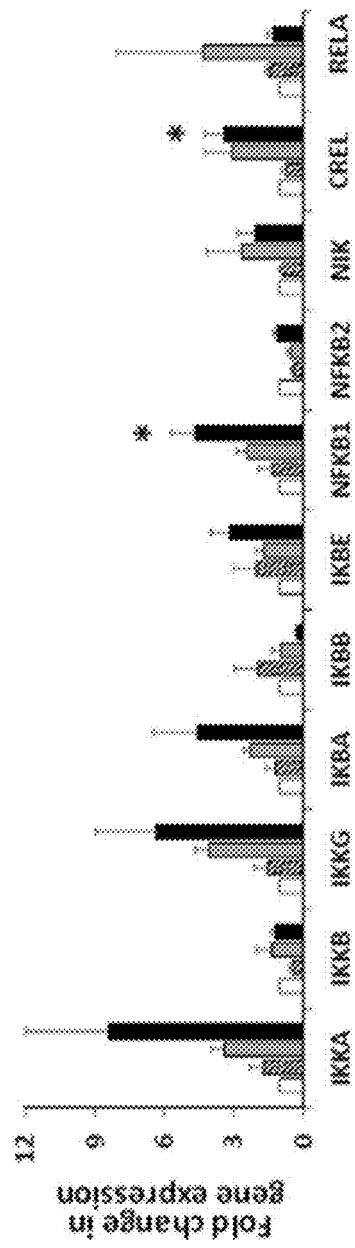

Transfusion-Associated NEC-Like Injury Activated Inflammatory Genes in Mouse Model To identify the inflammatory mediators involved in transfusion-associated NEC-like injury, quantitative PCR arrays focused on inflammatory cytokines, Toll-like receptor (TLR)-activated signaling, and the nuclear factor-kappa B (NF-κB) pathway (FIGS. 6A-6C). NEC-like injury induced interleukin-1β (Il1b), tumor necrosis factor (Tnf), monocyte chemokines CC-motif ligand (Ccl)-2, Ccl3, Ccl5, Cxcl5, Tlr4, myeloid differentiation primary response gene 88 (Myd88), Nfkb1, and the reticuloendotheliosis proto-oncogene, NF-κB subunit (Rel/Crel). The anemic intestine showed increased Tnf, Myd88, and Rel expression.

Example 8

Figure 7C:
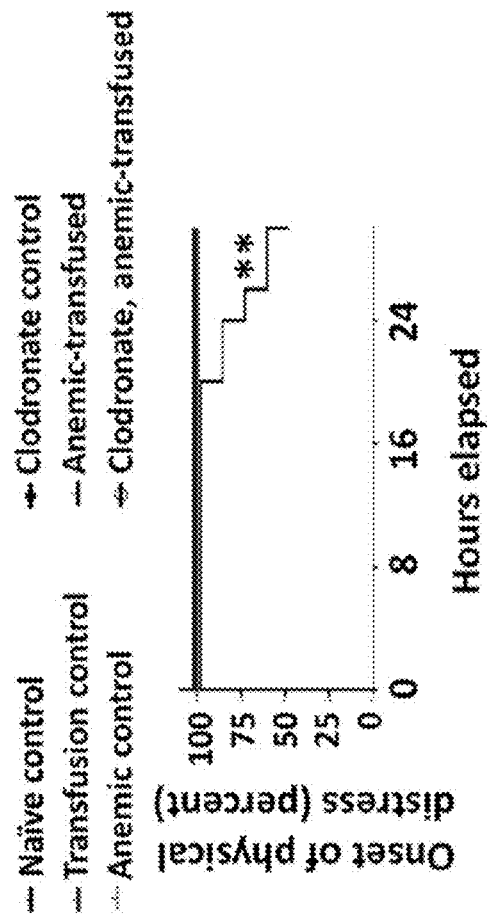
Figure 7D:
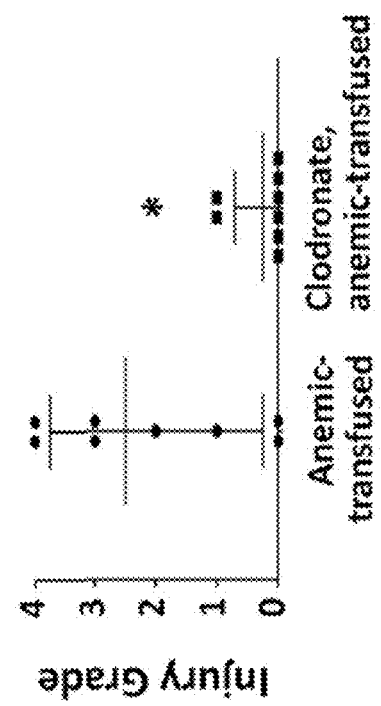

Macrophage Depletion Prevents Transfusion-Associated NEC-Like Injury in Mouse Model To ascertain the causative role of macrophages, some normal and anemic mouse pups were treated with clodronate on P8 to deplete monocytes and macrophages in the intestine (FIG. 7A). When RBC transfusions were administered per protocol on P11 in mice that had undergone macrophage depletion, these animals did not develop bowel injury (FIGS. 7B-7D).

Figure 7E:
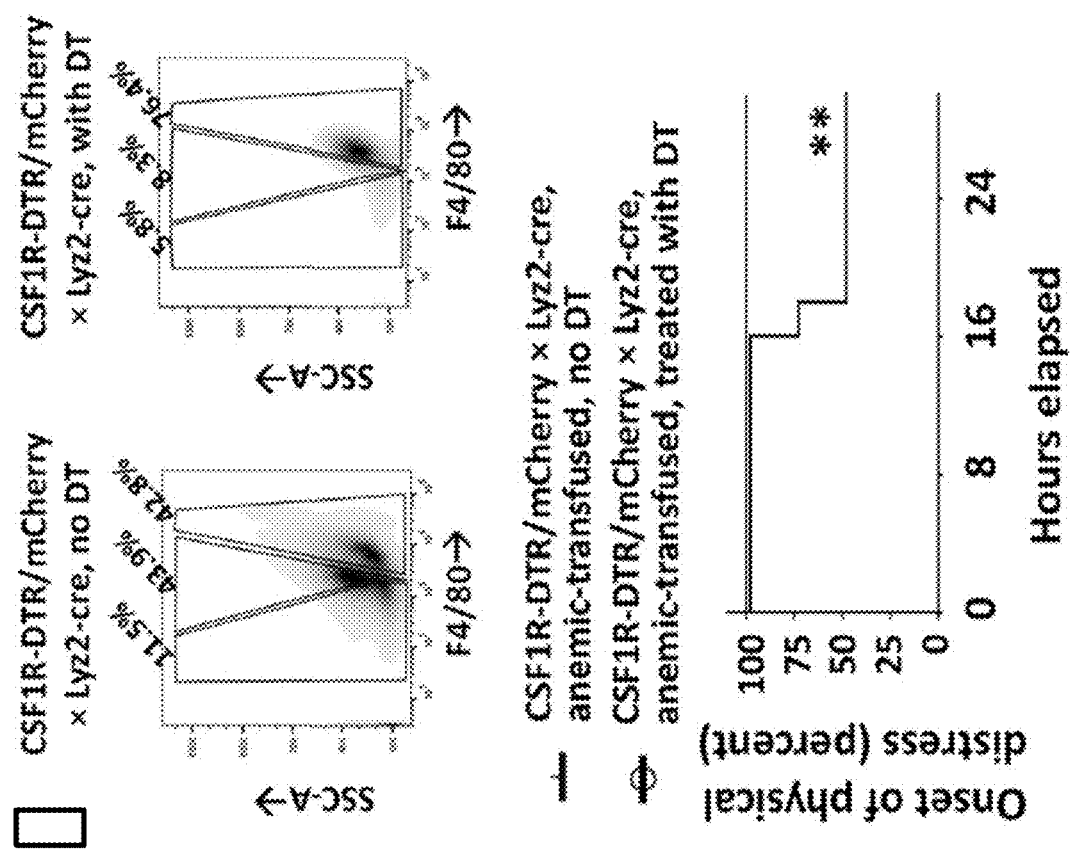
Figure 7F:
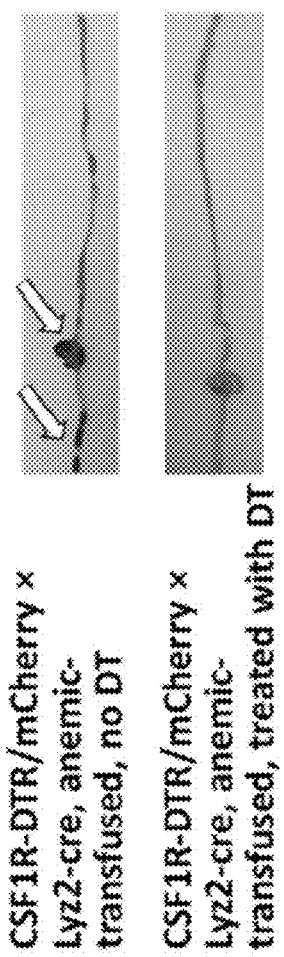
Figure 7G:
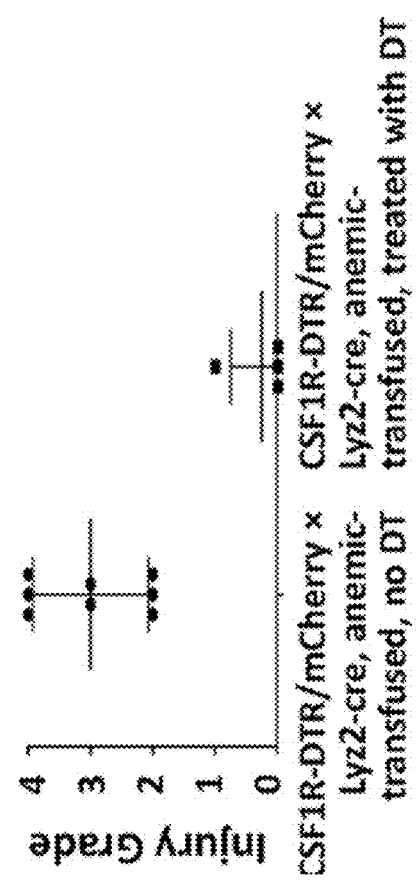

These findings were confirmed using a second, more specific approach for macrophage depletion. In this model, transgenic mice carrying a bacterial-artificial chromosome encoding a CD115 promoter-driven diphtheria toxin receptor-mCherry fusion protein (DTR-mCherry) that is preceded by a loxP-flanked transcriptional Stop element were used. Crossing these animals with Lyz2 (lysozyme 2)-cre mice deletes the floxed Stop element and allows expression of DTR-mCherry in inflammatory monocytes. In these pups, administration of diphtheria toxin (DT, 5 ng/g weight) selectively depleted the inflammatory F4/80mid CD115+ Ly6Chi macrophages but not the resident macrophages (FIG. 7E). Similar to the findings with clodronate, this selective depletion of inflammatory macrophages was also protective (FIGS. 7E-7G).

RBC transfusions activated inflammatory macrophages with increased production of secondary mediators such as ROS (FIG. 5), as described in Example 6, and inflammatory cytokines (FIG. 6), as described in Example 7, which likely mediated the transfusion-related tissue damage. In support of a reoxygenation-related mechanism, 4-hydroxynonenal (4-HNE) was detected in intestinal macrophages and in nearby epithelial cells, indicating ongoing ROS-mediated lipid peroxidation. However, 4-HNE seemed to be differentially expressed with a more robust fluorescence signal in macrophages than in the epithelium, indicating that ROS production may be specific to macrophages and should not be yet presumed to be a part of a generalized reoxygenation injury. The pathophysiological importance of macrophages was evident from the protection observed in studies with clodronate depletion, or in the transgenic mouse model with DT-mediated depletion of inflammatory macrophages. Blocking the inflammatory activation of intestinal macrophages was also protective, adding further support to this model.

Example 9

Figure 8A:
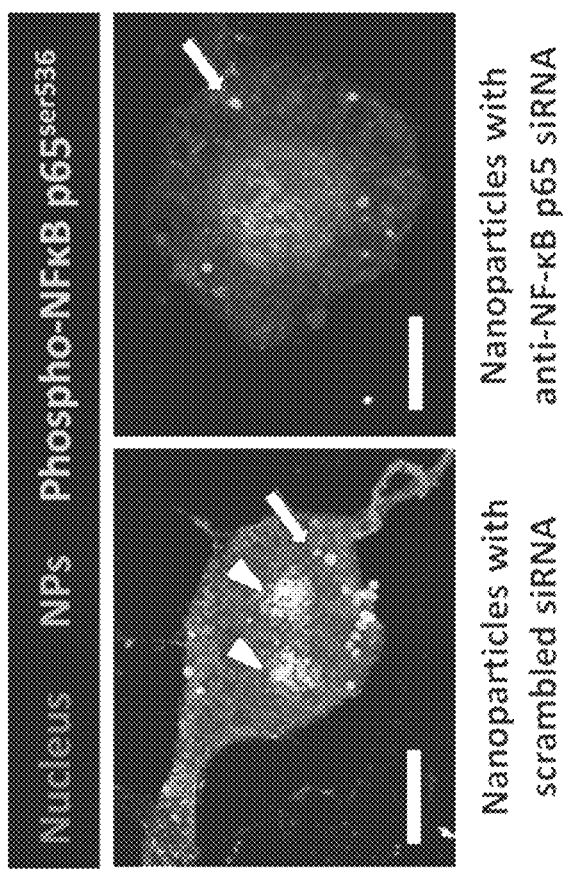
FIGS. 8A-8D show that macrophage activation is required for RBC transfusion-associated NEC-like injury. Scatter plots (means±SD) show relative NF-κB activity in reporter cells treated with nanoparticles (NP) containing siRNA against NF-κB p65, and then with 7-day RBCs (FIG. 8A). Controls included no NPs or NPs containing control (scrambled) siRNA; N=8 donors; Kruskal-Wallis H test with Dunn's post-test, † P<0.001. Fluorescence photomicrographs (magnification 2400×) show 'activated' appearance and nuclear translocation of phospho-NF-κB p65 (FIG. 8A, the light grey areas pointed by filled triangles) in a macrophage treated with control NPs. Cells treated with anti-p65 NPs did not show phospho-NF-κB p65. Arrows indicate NPs (FIG. 8A). Scale bar 5 μm. Kaplan-Meier curves show onset of NEC-like injury in anemic-transfused pups treated with control or anti-p65 NPs (FIG. 8B). Treatment with anti-p65 siRNA was protective; Mantel-Cox log-rank test, † P<0.001. Photographs show the injured intestine from an anemic-transfused pup treated with control NPs (FIG. 8C, arrows) but no injury in a pup treated with NPs containing anti-p65 siRNA. Scatter plots (FIG. 8C, below) summarize the severity of bowel injury in the two groups. N=6 anemic-transfused mice treated with control NPs, 11 anemic-transfused treated with anti-p65 NPs; Mann-Whitney U test, † P<0.001. Fluorescence photomicrographs (magnification 400×) of proximal colon from anemic-transfused mice treated with either control or anti-p65 NPs show immunoreactivity for Ly6C (FIG. 8D, filled triangles), fluorescence tag on NPs (FIG. 8D, open triangles), and phospho-NF-κB (FIG. 8D, dashed arrows). Mice treated with control NPs show tissue damage and nuclear translocation of phospho-p65, whereas those treated with anti-p65 NPs show preserved histoarchitecture and no immunoreactivity for phospho-p65 in Ly6C+ macrophages. Cytoplasmic staining for phospho-p65 was seen in 2 cells (FIG. 8D, open arrows), which did not co-localize with Ly6C. Scale bar 50 μm; Data represent sections stained from 5 mice per group.
Figure 8A:
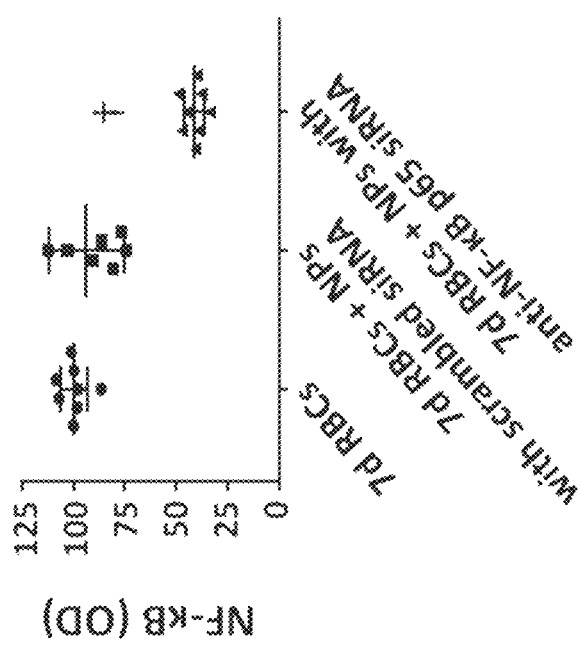
Figures 8B, 8C:
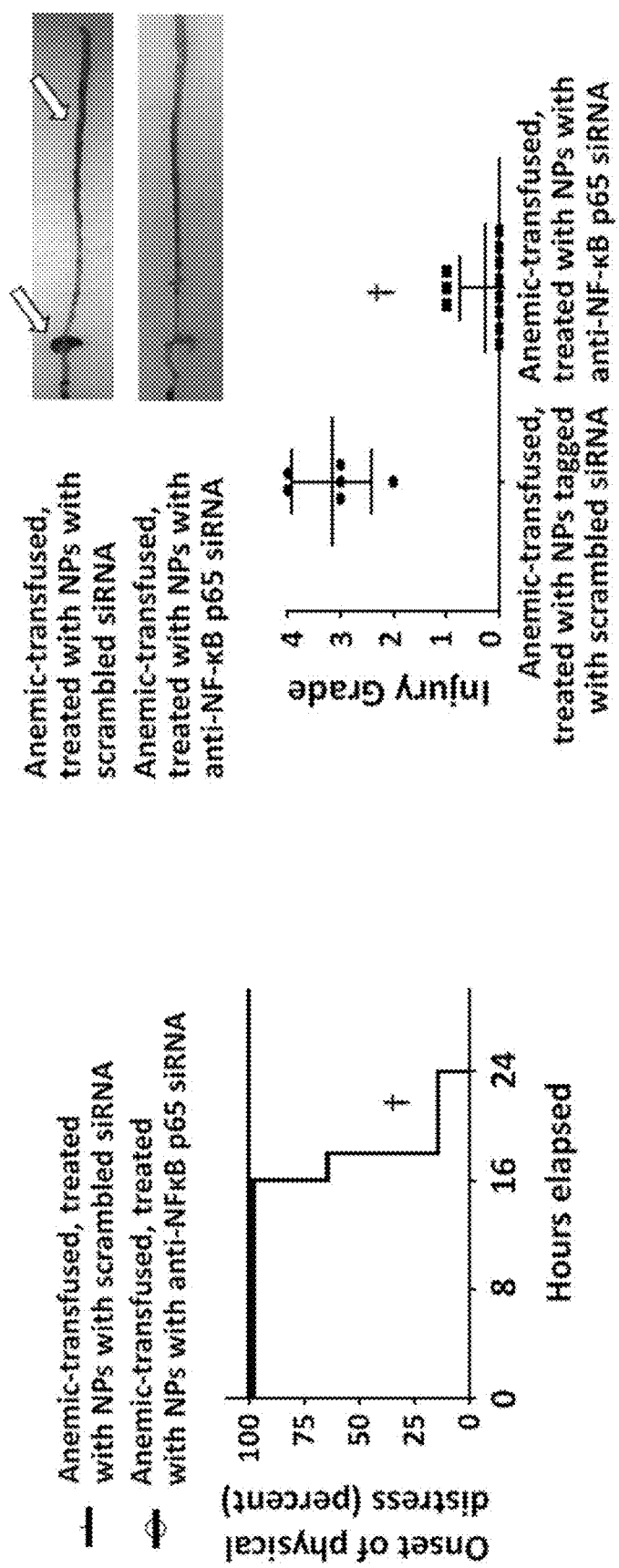
Figure 8D:
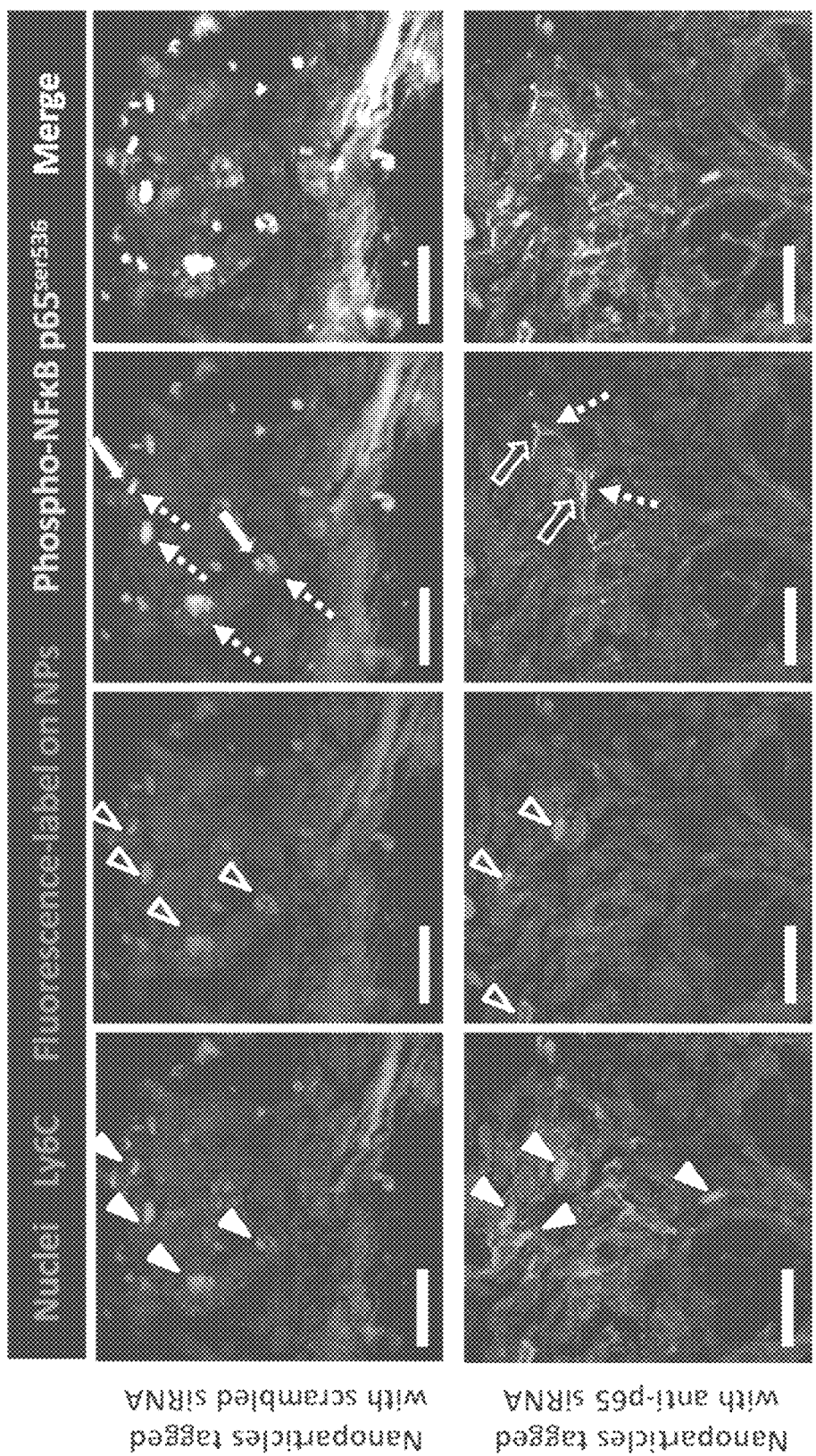

Macrophage Activation is Required for RBC Transfusion-Associated NEC-Like Injury in Mouse Model To determine whether the inflammatory activation of macrophages in the anemic intestine was essential for transfusion-associated bowel injury, an established, nanoparticle-based approach to block the NF-κB pathway in macrophages in vivo was used. These nanoparticles are comprised of a fluorescence tagged small-interfering ribonucleic acid (siRNA) targeting the NF-κB p65 transcript, in complex with a melittin (principal component of bee venom)-derived cationic amphipathic peptide that improves siRNA delivery by initiating endosomal escape. The efficiency of these nanoparticles was first tested in vitro by treating NF-κB reporter macrophages with nanoparticles containing either scrambled or anti-p65 siRNA for 24 hrs before stimulating these cells with 7-day-stored RBCs. These nanoparticles were readily phagocytosed by the macrophages, and nanoparticles containing anti-p65 siRNA specifically blocked NF-κB activation following exposure to stored RBCs (FIG. 8A). These nanoparticles were then administered to anemic mice (1 nmol intravenously, 2 nmol intraperitoneal; pre-determined optimum) 24 hrs prior to the RBC transfusion. These nanoparticles are preferentially phagocytosed by immune cells at sites of inflammation. Mice treated with anti-p65 nanoparticles were protected (FIGS. 8B-8C). Fluorescence photomicrographs (FIG. 8D) showed Ly6C+ macrophages in the anemic-transfused mice treated with nanoparticles containing either control or anti-p65 siRNA. In control, Ly6C+ macrophages showed fluorescence from the Cy3-tag on siRNA in the nanoparticles, but also showed nuclear translocation of phosphorylated NF-κB p65. In mice that received nanoparticles with anti-NF-κB p65 siRNA, Ly6C+ macrophages were detected but without phosphorylation or nuclear translocation of NF-κB p65.

Example 10

Figure 9B:
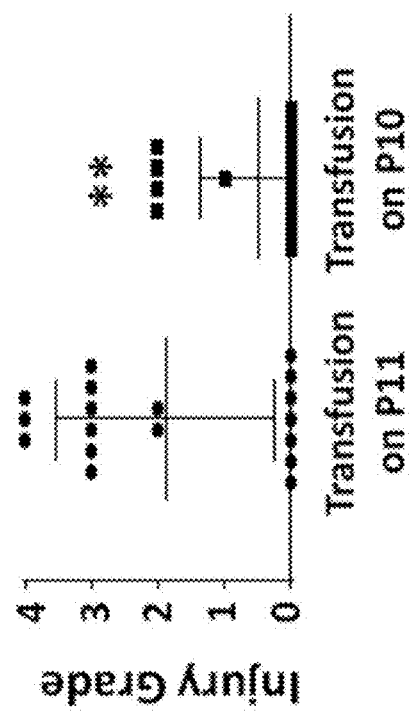
FIGS. 9A-9I show clinically-relevant variables in transfusion-associated NEC-like injury. Scatter plots show severity of NEC-like injury following: RBC transfusions in mice with severe (hematocrit 20-24%) vs. moderate anemia (hematocrit 25-30%) (FIG. 9A); transfusions administered soon after the hematocrit dropped to 20-24% (on P10) vs. 24 hrs later (P11) (FIG. 9B); transfusions with leukoreduced, packed RBCs vs. RBCs that were leukoreduced, washed, and resuspended in PBS before storage (FIG. 9C); transfusions with RBCs stored for 7 vs. 14 days (FIG. 9D); single vs. multiple RBC transfusions (FIG. 9E); and with allogeneic (from FVB/NJ mice) vs. syngeneic RBCs (from C57BL/6) (FIG. 9F). N=18 mice/group; Mann-Whitney U test, * P<0.05, ** P<0.01, † P<0.001. Scatter plot shows positive correlation (Spearman's r=0.865) between number of transfusions and severity of injury (FIG. 9G); † P<0.001.
Figure 9A:
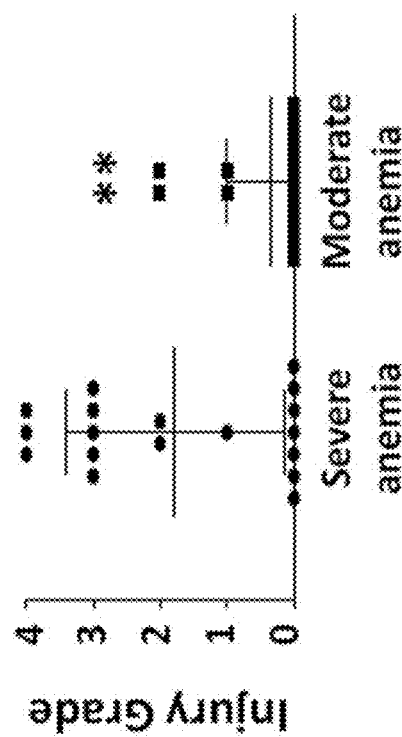

Clinically-Relevant Variables in RBC Transfusion-Associated NEC-Like Injury in Mouse Model Mice were monitored to determine if the risk/severity of transfusion-associated NEC-like injury was affected by the severity of anemia prior to the transfusion. RBC transfusions triggered NEC-like injury in 11/18 mice with severe anemia (hematocrit 20-24%) but only in 4/18 with moderate anemia (hematocrit 25-30%; p=0.04, Fisher's exact test). The severity of bowel injury was higher in the severely-anemic mice (FIG. 9A). Whether the time spent in a severely-anemic state increased the risk/severity of transfusion-associated NEC-like injury was questioned. Mice transfused on P10 sustained less bowel damage than those transfused on P11, which had been severely anemic for 24 hrs (FIG. 9B). Bowel injury was recorded in 5/18 pups that were transfused on P10 vs. 12/18 mice transfused on P11 (p=0.04).

Figure 9D:
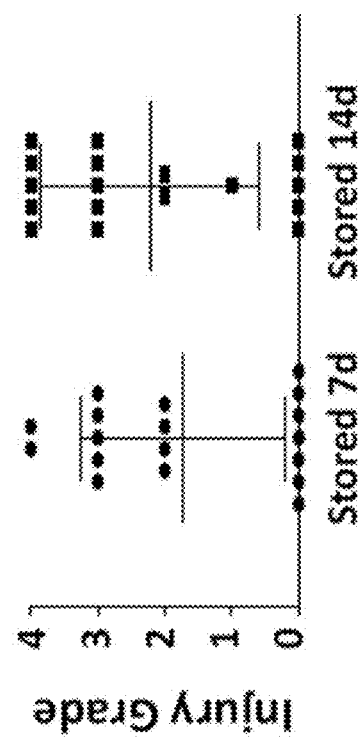
Figure 9C:
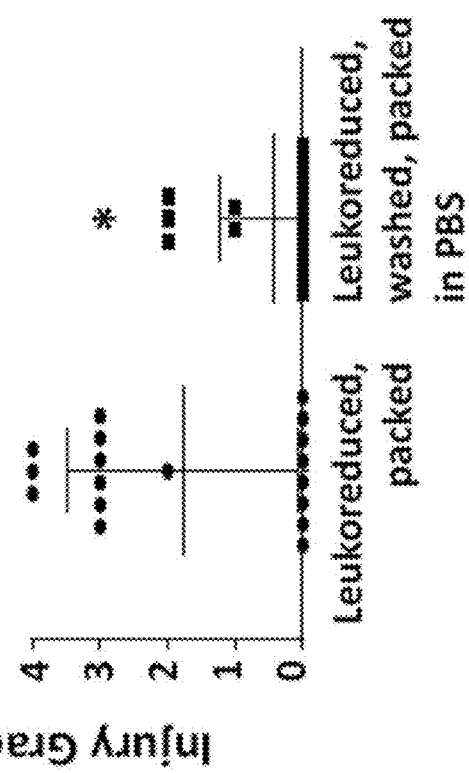
Figure 9F:
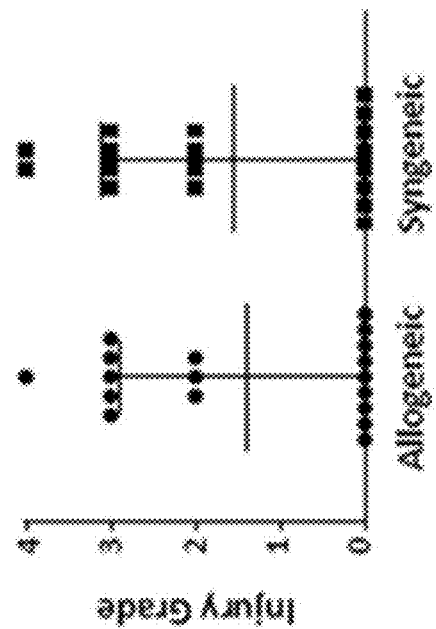

In most experiments, mice were transfused with packed, leukoreduced RBCs. However, in view of the inflammatory effects of soluble factors present in the plasma supernatant from stored RBCs (FIG. 5A), the protective effect of the removal of the plasma fraction was tested. Indeed, when RBCs were leukoreduced, washed, and resuspended and packed in PBS prior to storage, the severity of bowel injury was decreased (FIG. 9C). The frequency of bowel injury did not change significantly. RBC storage duration (7 days vs. 14 days) did not show a significant change in bowel injury (FIG. 9D). There was no difference between allogeneic (adult FVB/NJ donors, C57BL/6 recipient pups) vs. syngeneic transfusions (adult C57BL/6 donors, C57BL/6 recipient pups; FIG. 9F).

Figure 9E:
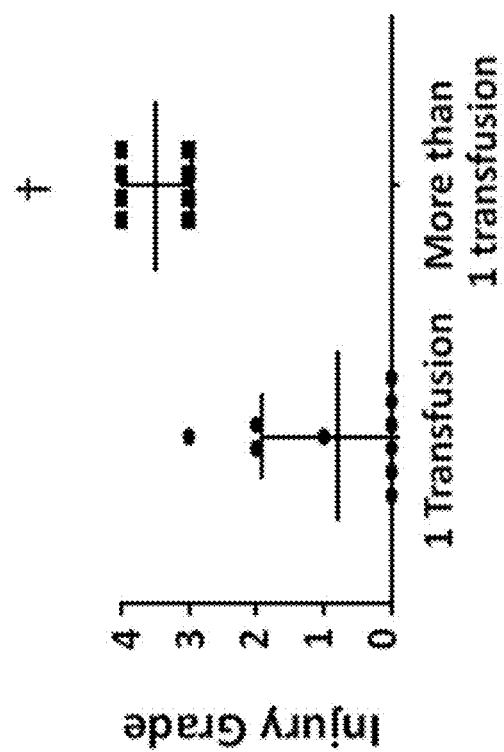
Figure 9G:
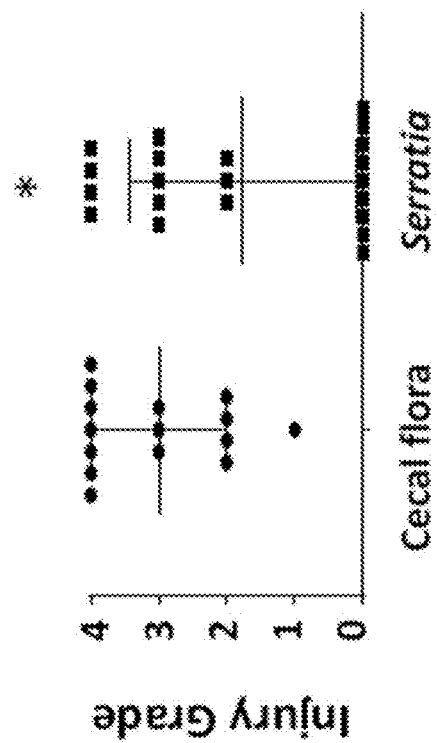
Figure 9H:
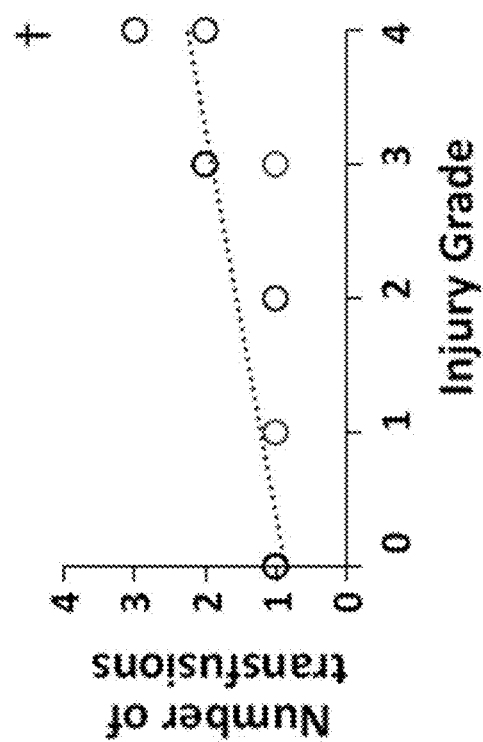
Figure 9I:
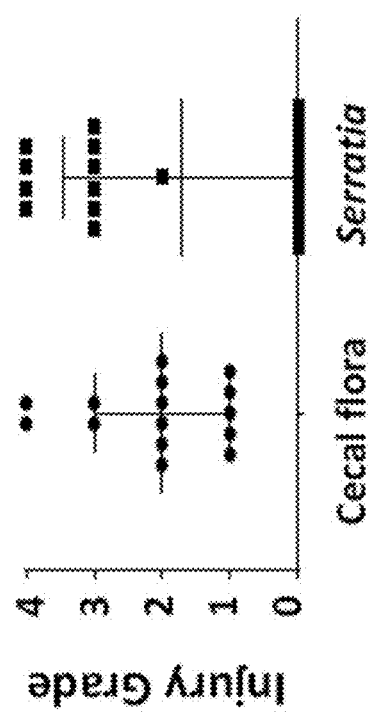

The potential for multiple RBC transfusions to increase the risk of bowel injury was tested. In the experimental protocol, the hematocrit was measured on P12 and P13, and if the hematocrit was <30%, these pups were transfused again with 20 mL/kg RBCs to try and achieve a hematocrit above 35%. These pups showed more severe injury (FIG. 9E). The severity of bowel injury also showed a significant correlation with the total number of RBC transfusions (r=0.865, p<0.001; FIG. 9G). Finally, the contribution of enteral Gram-negative flora to transfusion-associated NEC was tested. Increasing information indicates that infants who develop NEC may display enteric dysbiosis with increased Gammaproteobacteria in the days/weeks preceding NEC. To investigate the contribution of these *Serratia* to bowel injury, bowel injury was compared in these pups vs. mice given adult cecal flora that contained scant Gammaproteobacteria. There was no difference in the frequency of bowel injury, but interestingly, pups colonized with adult cecal flora sustained more severe ileal injury than the *Serratia*-colonized animals (FIG. 9H). Colonic injury was comparable in both groups (FIG. 9I). Enteral *Serratia* increased the expression of Il6 and Cxcl2, but did not alter the Toll-like receptors.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

For reasons of completeness, various aspects of the invention are set out in the following numbered clauses:

Clause 1. A method for generating a murine model of neonatal necrotizing enterocolitis, the method comprising: inducing anemia in a murine animal to generate an anemic murine animal; and administering at least one transfusion of red blood cells to the anemic murine animal, whereby the anemic murine animal exhibits at least one symptom of neonatal necrotizing enterocolitis.

Clause 2. The method of clause 1, wherein inducing anemia in the murine animal comprises administering at least one phlebotomy to the murine animal between postnatal day 2 and 10.

Clause 3. The method of clause 2, wherein between 3 and 6 phlebotomies are administered to the murine animal.

Clause 4. The method of clause 2 or 3, wherein at least 5 phlebotomies are administered to the murine animal.

Clause 5. The method of clause 3 or 4, wherein the phlebotomies are administered separately by at least one day from each other.

Clause 6. The method of any one of clauses 3-5, wherein the phlebotomies are administered at postnatal days 2, 4, 6, 8, and 10.

Clause 7. The method of any one of clauses 1-6, wherein between 1 and 3 transfusions of red blood cells are administered to the anemic murine animal.

Clause 8. The method of any one of clauses 1-7, wherein at least one transfusion of red blood cells is administered to the anemic murine animal on or after postnatal day 10.

Clause 9. The method of clause 8, wherein at least one transfusion of red blood cells is administered to the anemic murine animal on postnatal day 11.

Clause 10. The method of any one of clauses 1-9, wherein the red blood cells comprise leukoreduced red blood cells.

Clause 11. The method of any one of clauses 1-10, wherein the anemic murine animal has a hematocrit less than 30% prior to the at least one transfusion of red blood cells.

Clause 12. The method of any one of clauses 1-11, wherein the anemic murine animal has a hematocrit equal to or greater than 30% after the at least one transfusion of red blood cells.

Clause 13. The method of any one of clauses 1-12, further comprising introducing gut bacteria to the anemic murine animal prior to administering the at least one transfusion of red blood cells.

Clause 14. The method of any one of clauses 1-13, wherein the at least one symptom of neonatal necrotizing enterocolitis comprises inflammation of intestinal mucosa or epithelia, macrophage infiltration of intestinal mucosa, intestinal mucosal lesions, intestinal coagulation necrosis, intestinal interstitial hemorrhages, intestinal crypt villus disruption, focal intestinal epithelia disruption, induction of inflammatory markers or cytokines, other bowel injury, or combinations thereof.

Clause 15. A method to measure transfusion effects on anemia in a murine model, the method comprising: inducing anemia in a murine animal to generate an anemic murine animal; administering at least one transfusion of red blood cells to the anemic murine animal, whereby the murine animal exhibits at least one symptom of neonatal necrotizing enterocolitis; and measuring at least one of inflammatory markers or cytokines, intestinal mucosa or epithelia inflammation, macrophage infiltration of intestinal mucosa, intestinal mucosal lesions, intestinal coagulation necrosis, intestinal interstitial hemorrhages, intestinal crypt villus disruption, focal intestinal epithelia disruption, other bowel injury, or combinations thereof, before and after the transfusion of red blood cells thereby measuring the effects of transfusion on anemia.

Clause 16. A method for identifying and isolating an agent useful for the prevention of neonatal necrotizing enterocolitis, the method comprising: inducing anemia in a murine animal to generate an anemic murine animal; administering a candidate agent to the anemic murine animal thereby generating a treated anemic murine animal; administering at least one transfusion of red blood cells to the treated anemic murine animal, whereby the treated anemic murine animal exhibits at least one symptom of neonatal necrotizing enterocolitis; measuring at least one neonatal necrotizing enterocolitis symptoms in the treated anemic murine animal and identifying the candidate agent as useful for the prevention of neonatal necrotizing enterocolitis when the neonatal necrotizing enterocolitis symptom in the treated anemic murine animal are improved or delayed in the treated anemic murine animal, as compared to an untreated anemic murine animal that has been administered a transfusion of red blood cells, and wherein the at least one neonatal necrotizing enterocolitis symptoms comprises intestinal mucosa or epithelia inflammation, macrophage infiltration of intestinal mucosa, intestinal mucosal lesions, intestinal coagulation necrosis, intestinal interstitial hemorrhages, intestinal crypt villus disruption, focal intestinal epithelia disruption, other bowel injury, or combinations thereof.

Clause 17. A murine animal exhibiting at least one symptom of neonatal necrotizing enterocolitis produced by the method of any one of clauses 1-14.

Clause 18. The murine animal of clause 17, wherein the at least one symptom of neonatal necrotizing enterocolitis comprises inflammation of intestinal mucosa or epithelia, macrophage infiltration of intestinal mucosa, intestinal mucosal lesions, intestinal coagulation necrosis, intestinal interstitial hemorrhages, intestinal crypt villus disruption, focal intestinal epithelia disruption, induction of inflammatory markers or cytokines, other bowel injury, or combinations thereof.

Clause 19. A method for identifying an agent for treating neonatal necrotizing enterocolitis, the method comprising: administering a candidate agent to the murine animal of clause 17 or 18; measuring at least one symptom of neonatal necrotizing enterocolitis symptoms before and after the candidate agent is administered to the murine animal, wherein the at least one symptom of neonatal necrotizing enterocolitis symptoms comprises intestinal mucosa or epithelia inflammation, macrophage infiltration of intestinal mucosa, intestinal mucosal lesions, intestinal coagulation necrosis, intestinal interstitial hemorrhages, intestinal crypt villus disruption, focal intestinal epithelia disruption, other bowel injury, or combinations thereof; and identifying the candidate agent as useful for treating neonatal necrotizing enterocolitis when there is an improvement in the neonatal necrotizing enterocolitis symptom after the candidate agent is administered to the murine animal.

Clause 20. The method of clause 19, wherein the improvement in any of the neonatal necrotizing enterocolitis symptoms comprises a decrease in at least one of inflammatory markers, cytokines, intestinal mucosa or epithelia inflammation, macrophage infiltration of intestinal mucosa, intestinal mucosal lesions, intestinal coagulation necrosis, intestinal interstitial hemorrhages, intestinal crypt villus disruption, focal intestinal epithelia disruption, other bowel injury, or combinations thereof.

Clause 21. The method of any one of clauses 1-20, wherein the murine animal is a mouse.

What is claimed is:

1. A method for generating a murine model of neonatal necrotizing enterocolitis, the method comprising: inducing anemia in a neonatal murine animal to generate an anemic neonatal murine animal; and administering at least one transfusion of red blood cells to the anemic neonatal murine animal, whereby the anemic neonatal murine animal exhibits at least one symptom of neonatal necrotizing enterocolitis.

2. The method of claim 1, wherein inducing anemia in the neonatal murine animal comprises administering at least one phlebotomy to the murine animal between postnatal day 1 and 11.

3. The method of claim 2, wherein between about 2 and 7 phlebotomies are administered to the neonatal murine animal.

4. The method of claim 3, wherein the phlebotomies are administered separately by at least one day from each other.

5. The method of claim 3, wherein the phlebotomies are administered at postnatal days 2, 4, 6, 8, and 10.

6. The method of claim 1, wherein between about 1 and 4 transfusions of red blood cells are administered to the anemic neonatal murine animal.

7. The method of claim 1, wherein at least one transfusion of red blood cells is administered to the anemic neonatal murine animal on or after postnatal day 10.

8. The method of claim 7, wherein at least one transfusion of red blood cells is administered to the anemic neonatal murine animal on postnatal day 11.

9. The method of claim 1, wherein the red blood cells comprise leukoreduced red blood cells.

10. The method of claim 1, wherein the anemic neonatal murine animal has a hematocrit less than approximately 30% prior to the at least one transfusion of red blood cells.

11. The method of claim 1, wherein the anemic neonatal murine animal has a hematocrit equal to or greater than 30% after the at least one transfusion of red blood cells.

12. The method of claim 11, further comprising introducing gut bacteria to the anemic neonatal murine animal prior to administering the at least one transfusion of red blood cells.

13. The method of claim 1, wherein the at least one symptom of neonatal necrotizing enterocolitis comprises inflammation of intestinal mucosa or epithelia, macrophage infiltration of intestinal mucosa, intestinal mucosal lesions, intestinal coagulation necrosis, intestinal interstitial hemorrhages, intestinal crypt villus disruption, focal intestinal epithelia disruption, induction of inflammatory markers or cytokines, or combinations thereof.

14. The method of claim 1, wherein the neonatal murine animal is a mouse.

* * * * *